(12) United States Patent
Kramer et al.

(10) Patent No.: US 8,798,747 B2
(45) Date of Patent: *Aug. 5, 2014

(54) METHOD AND APPARATUS FOR CONTROL OF CARDIAC THERAPY USING NON-INVASIVE HEMODYNAMIC SENSOR

(75) Inventors: Andrew P. Kramer, Marine on St. Croix, MN (US); Joseph M. Pastore, Concord, OH (US); Jeffrey E. Stahmann, Ramsey, MN (US); Rodney W. Salo, Fridley, MN (US); Jesse W. Hartley, White Bear Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 299 days.

This patent is subject to a terminal disclaimer.

(21) Appl. No.: 13/273,108

(22) Filed: Oct. 13, 2011

(65) Prior Publication Data

US 2012/0029588 A1 Feb. 2, 2012

Related U.S. Application Data

(63) Continuation of application No. 11/315,032, filed on Dec. 22, 2005, now Pat. No. 8,046,069.

(51) Int. Cl.
*A61N 1/00* (2006.01)
(52) U.S. Cl.
USPC .......................................................... 607/17
(58) Field of Classification Search
USPC ........... 600/483, 500–503; 607/17–18, 22–23
See application file for complete search history.

(56) References Cited

U.S. PATENT DOCUMENTS

| 4,519,395 | A | 5/1985 | Hrushesky |
|---|---|---|---|
| 4,922,907 | A | 5/1990 | Hedin et al. |
| 4,930,518 | A | 6/1990 | Hrushesky |
| 5,156,147 | A | 10/1992 | Warren et al. |
| 5,168,869 | A | 12/1992 | Chirife |
| 5,188,106 | A | 2/1993 | Nappholz et al. |
| 5,197,467 | A | 3/1993 | Steinhaus et al. |
| 5,291,895 | A | 3/1994 | McIntyre |
| 5,312,452 | A | 5/1994 | Salo |
| 5,318,595 | A | 6/1994 | Ferek-Petric et al. |
| 5,330,511 | A | 7/1994 | Boute |

(Continued)

FOREIGN PATENT DOCUMENTS

| DE | 19720755 | 11/1998 |
|---|---|---|
| EP | 0474958 A2 | 3/1992 |

(Continued)

OTHER PUBLICATIONS

"European Application Serial No. 06837544.3, Brief Communication dated Nov. 17, 2011", 7 pgs.

(Continued)

*Primary Examiner* — Mark W Bockelman
(74) *Attorney, Agent, or Firm* — Schwegman Lundberg & Woessner, P.A.

(57) ABSTRACT

A cardiac rhythm management (CRM) system includes a non-invasive hemodynamic sensing device and an implantable medical device to sense a hemodynamic signal and derive one or more cardiac performance parameters from the hemodynamic signal. The non-invasive hemodynamic sensing device includes at least a portion configured for external attachment to a body in which the implantable medical device is implanted. The one or more cardiac performance parameters are used for various diagnostic, monitoring, and therapy control purposes.

20 Claims, 20 Drawing Sheets

(56) References Cited

U.S. PATENT DOCUMENTS

| | | |
|---|---|---|
| 5,334,222 A | 8/1994 | Salo et al. |
| 5,409,009 A | 4/1995 | Olson |
| 5,413,592 A | 5/1995 | Schroeppel |
| 5,417,717 A | 5/1995 | Salo et al. |
| 5,454,838 A | 10/1995 | Vallana et al. |
| 5,466,245 A | 11/1995 | Spinelli et al. |
| 5,487,752 A | 1/1996 | Salo et al. |
| 5,514,163 A | 5/1996 | Markowitz et al. |
| 5,527,347 A | 6/1996 | Shelton et al. |
| 5,534,016 A | 7/1996 | Boute |
| 5,540,727 A | 7/1996 | Tockman et al. |
| 5,544,661 A | 8/1996 | Davis et al. |
| 5,549,650 A | 8/1996 | Bornzin et al. |
| 5,554,177 A | 9/1996 | Kieval et al. |
| 5,562,711 A | 10/1996 | Yerich et al. |
| 5,578,064 A | 11/1996 | Prutchi |
| 5,609,612 A | 3/1997 | Plicchi et al. |
| 5,626,620 A | 5/1997 | Kieval et al. |
| 5,626,623 A | 5/1997 | Kieval et al. |
| 5,628,777 A | 5/1997 | Moberg et al. |
| 5,674,256 A | 10/1997 | Carlson |
| 5,690,689 A | 11/1997 | Sholder |
| 5,700,283 A | 12/1997 | Salo |
| 5,707,400 A | 1/1998 | Terry, Jr. et al. |
| 5,713,930 A | 2/1998 | van der Veen et al. |
| 5,713,933 A | 2/1998 | Condie et al. |
| 5,716,383 A | 2/1998 | Kieval et al. |
| 5,749,900 A | 5/1998 | Schroeppel et al. |
| 5,749,906 A | 5/1998 | Kieval et al. |
| 5,800,471 A | 9/1998 | Baumann |
| 5,819,740 A | 10/1998 | Muhlenberg |
| 5,836,975 A | 11/1998 | DeGroot |
| 5,836,987 A | 11/1998 | Baumann et al. |
| 5,891,176 A | 4/1999 | Bornzin |
| 6,058,329 A | 5/2000 | Salo et al. |
| 6,070,100 A | 5/2000 | Bakels et al. |
| 6,144,878 A | 11/2000 | Schroeppel et al. |
| 6,144,880 A | 11/2000 | Ding et al. |
| 6,155,267 A | 12/2000 | Nelson |
| 6,208,901 B1 | 3/2001 | Hartung |
| 6,223,082 B1 | 4/2001 | Bakels et al. |
| 6,280,389 B1 | 8/2001 | Ding et al. |
| 6,311,089 B1 | 10/2001 | Mann et al. |
| 6,371,922 B1 | 4/2002 | Baumann et al. |
| 6,398,734 B1 | 6/2002 | Cimochowski et al. |
| 6,409,675 B1 | 6/2002 | Turcott |
| 6,430,439 B1 | 8/2002 | Wentkowski et al. |
| 6,438,421 B1 | 8/2002 | Stahmann et al. |
| 6,449,510 B1 | 9/2002 | Albers et al. |
| 6,480,733 B1 | 11/2002 | Turcott |
| 6,480,742 B2 | 11/2002 | Stahmann et al. |
| 6,491,639 B1 | 12/2002 | Turcott |
| 6,507,756 B1 | 1/2003 | Heynen et al. |
| 6,512,952 B2 | 1/2003 | Stahmann et al. |
| 6,522,921 B2 | 2/2003 | Stahmann et al. |
| 6,522,923 B1 | 2/2003 | Turcott |
| 6,527,729 B1 | 3/2003 | Turcott |
| 6,553,258 B2 | 4/2003 | Stahmann et al. |
| 6,597,951 B2 | 7/2003 | Kramer et al. |
| 6,600,949 B1 | 7/2003 | Turcott |
| 6,665,564 B2 | 12/2003 | Lincoln et al. |
| 6,832,113 B2 | 12/2004 | Belalcazar |
| 6,963,777 B2 | 11/2005 | Lincoln et al. |
| 7,206,636 B1 | 4/2007 | Turcott |
| 7,231,248 B2 | 6/2007 | Kramer et al. |
| 7,366,569 B2 | 4/2008 | Belalcazar |
| 8,046,069 B2 | 10/2011 | Kramer et al. |
| 2001/0047194 A1 | 11/2001 | Thompson et al. |
| 2002/0133198 A1 | 9/2002 | Kramer et al. |
| 2002/0143264 A1 | 10/2002 | Ding et al. |
| 2003/0097158 A1 | 5/2003 | Belalcazar |
| 2003/0105496 A1 | 6/2003 | Yu et al. |
| 2003/0199936 A1 | 10/2003 | Struble et al. |
| 2004/0220636 A1 | 11/2004 | Burnes |
| 2005/0038477 A1 | 2/2005 | Kramer et al. |
| 2005/0043767 A1 | 2/2005 | Belalcazar |
| 2005/0115561 A1 | 6/2005 | Stahmann et al. |
| 2006/0009818 A1 | 1/2006 | Von Arx et al. |
| 2006/0064133 A1 | 3/2006 | Von Arx et al. |
| 2007/0150014 A1 | 6/2007 | Kramer et al. |

FOREIGN PATENT DOCUMENTS

| | | |
|---|---|---|
| EP | 0793975 | 9/1997 |
| EP | 1962956 B1 | 5/2012 |
| JP | 9-192242 A | 7/1997 |
| WO | WO-2006008535 A1 | 1/2006 |
| WO | WO-2007073455 A1 | 6/2007 |

OTHER PUBLICATIONS

"European Application Serial No. 06837544.3, Office Action mailed Dec. 19, 2011", 6 pgs.

"European Application Serial No. 06837544.3, Response filed Oct. 20, 2011 to Summons to Attend Oral Hearings dated Jun. 1, 2011", 4 pgs.

"European Application Serial No. 06837544.3, Response filed Nov. 22, 2011 to Brief Communication mailed Nov. 17, 2011", 15 pgs.

"European Application Serial No. 11153443.4, Response filed Oct. 20, 2011 to Office Action mailed Apr. 27, 2011", 13 pgs.

"Japanese Application Serial No. 2008-547234, Office Action mailed Feb. 27, 2012", w/ English Translation, 7 pgs.

"Japanese Application Serial No. 2008-547234, Response filed May 28, 2012 to Office Action mailed Feb. 27, 2012", (w/ English Translation of Amended Claims), 8 pgs.

"Japanese Application Serial No. 2008-547234, Examiner Final Decision mailed Aug. 20, 2012", With English Translation, 6 pgs.

"U.S. Appl. No. 09/993,35, 312 Amendment mailed Oct. 12, 2004", 2 pgs.

"U.S. Appl. No. 09/993,351, Amendment Under 37 CFR Sec. 1.312(a) filed Sep. 2, 2004 to Notice of Allowance mailed Jun. 2, 2004", 13 pgs.

"U.S. Appl. No. 09/993,351, Non-Final Office Action mailed Jan. 12, 2004", 9 pgs.

"U.S. Appl. No. 09/993,351, Notice of Allowance mailed Jun. 2, 2004", 7 pgs.

"U.S. Appl. No. 09/993,351, Response filed Apr. 12, 2004 to Non-Final Office Action mailed Jan. 12, 2004", 18 pgs.

"U.S. Appl. No. 09/993,351, Supplemental Notice of Allowability mailed Aug. 30, 2004", 4 pgs.

"U.S. Appl. No. 10/941,427, Non-Final Office Action mailed Dec. 19, 2006", 6 pgs.

"U.S. Appl. No. 10/941,427, Non-Final Office Action mailed Jun. 6, 2007", 6 pgs.

"U.S. Appl. No. 10/941,427, Notice of Allowance mailed Dec. 11, 2007", NOAR, 7 pgs.

"U.S. Appl. No. 10/941,427, Response filed Mar. 5, 2007 to Non-Final Office Action mailed Dec. 19, 2006", 11 pgs.

"U.S. Appl. No. 10/941,427, Response filed Sep. 6, 2007 to Non-Final Office Action mailed Jun. 6, 2007", 10 pgs.

"U.S. Appl. No. 11/315,032, Advisory Action mailed May 10, 2011", 3 pgs.

"U.S. Appl. No. 11/315,032, Final Office Action mailed Feb. 14, 2011", 10 pgs.

"U.S. Appl. No. 11/315,032, Non-Final Office Action mailed Jun. 25, 2009", 5 pgs.

"U.S. Appl. No. 11/315,032, Notice of Allowance mailed Jul. 1, 2011".

"U.S. Appl. No. 11/315,032, Response filed Mar. 8, 2010 to Restriction Requirement mailed Feb. 4, 2010", 13 pgs.

"U.S. Appl. No. 11/315,032, Response filed Sep. 25, 2009 to Non Final Office Action mailed Jun. 25, 2009", 17 pgs.

"U.S. Appl. No. 11/315,032, Response filed Apr. 14, 2011 to Final Office Action mailed Feb. 14, 2011", 16 pgs.

"U.S. Appl. No. 11/315,032, Response filed Jun. 14, 2011 to Advisory Action mailed Feb. 14, 2011", 16 pgs.

"U.S. Appl. No. 11/315,032, Restriction Requirement mailed Feb. 4, 2010", 6 pgs.

(56) References Cited

OTHER PUBLICATIONS

"European Application Serial No. 06837544.3, Office Action mailed Feb. 6, 2009", 5 pgs.
"European Application Serial No. 11153443.4, Extended European Search Report mailed Mar. 14, 2011", 6 pgs.
"European Application Serial No. 06837544.3, Summons to Attend Oral Proceedings mailed Jun. 1, 2011", 5.
"International Search Report for corresponding PCT Application Serial No. PCT/US2006/044160", (Mar. 14, 2007), 5 pgs.
"Itamar Medical and Medtronic Announce Further Cooperation to Advance Diagnostic Innovation", Business Wire, p. 1254, Full text provided by Dialog, (May 9, 2000), 2 pgs.
"Noninvasive MIKRO-TIP Pulse Pressure Transducer Model SPT-301", Millar Instruments, Inc., Product Information, (2000), 1 pg.
"Written Opinion for corresponding PCT Application Serial No. PCT/US2006/044160", (Mar. 14, 2007), 7 pgs.
Butter, C., et al., "Cardiac resynchronization therapy optimization by finger plethysmography.", Heart Rhythm, 1(5), (Nov. 2004), 568-75.
Cazeau, S., et al., "Multisite stimulation for correction of cardiac asynchrony", Heart, 84(6), (Dec. 2000), 579-81.
Kass, David A, "Improved Left Ventricular Mechanics From Acute VDD Pacing in Patients with Dilated Cardiomyopathy and Ventricular Conduction Delay", Circulation, 99(12), (Mar. 30, 1999), 1567-1573.
Kramer, Andrew P, "Automatic Selection From Multiple Cardiac Optimization Protocols", U.S. Appl. No. 10/624,458, filed Jul. 21, 2003, 49 pgs.
McIntyre, K. M., et al., "A noninvasive method of predicting pulmonary-capillary wedge pressure", N Engl J Med., 327(24), (Dec. 10, 1992), 1715-20.
Ritter, P., et al., "A Built-In System Based on the Peak Endocardial Acceleration (PEA) for AV-Delay Optimization in DDDR Pacing", PACE, 20(5) (Part II), (Abstract of Paper presented at EUROPACE '97), (May 1997), 1567.
Ritter, P., et al., "Determination of the optimal atrioventricular delay in DDD pacing. Comparison between echo and peak endocardial acceleration measurements", Europace, 1(2), (Apr. 1999), 126-130.
Ritter, P., et al., "New Method for Determining the Optimal Atrio-Ventricular Delay in Patients Paces in DDD Mode for Complete Atrio-Ventricular Block", Pace, 18, Abstact No. 237, (Apr. 1995), 855.

METHOD AND APPARATUS FOR CONTROL OF CARDIAC THERAPY USING NON-INVASIVE HEMODYNAMIC SENSOR

CLAIM OF PRIORITY

This application is a continuation of and claims the benefit of priority under 35 U.S.C. 120 to U.S. patent application Ser. No. 11/315,032, filed on Dec. 22, 2005, now issued as U.S. Pat. No. 8,046,069, which is hereby incorporated by reference herein in its entirety.

CROSS-REFERENCE TO RELATED APPLICATIONS

This application is related to, commonly assigned, U.S. patent application Ser. No. 10/941,427, entitled "NON-INVASIVE METHOD AND APPARATUS FOR CARDIAC PACEMAKER PACING PARAMETER OPTIMIZATION AND MONITORING OF CARDIAC DYSFUNCTION," filed on Sep. 15, 2004, now issued as U.S. Pat. No. 7,366,569, which is hereby incorporated herein by reference in its entirety.

TECHNICAL FIELD

This document relates generally to cardiac rhythm management (CRM) systems and particularly, but not by way of limitation, to a system including a non-invasive sensor to sense a hemodynamic signal for cardiac performance monitoring and/or cardiac therapy control.

BACKGROUND

The heart is the center of a person's circulatory system. It includes an electro-mechanical system performing two major pumping functions. The left portions of the heart draw oxygenated blood from the lungs and pump it to the organs of the body to provide the organs with their metabolic needs for oxygen. The right portions of the heart draw deoxygenated blood from the body organs and pump it to the lungs where the blood gets oxygenated. These pumping functions are accomplished by cyclic contractions of the myocardium (heart muscles). In a normal heart, the sinoatrial node generates electrical impulses, called action potentials, at a normal sinus rate. The electrical impulses propagate through an electrical conduction system to various regions of the heart to excite the myocardial tissues of these regions. Coordinated delays in the propagations of the action potentials in a normal electrical conduction system cause the various portions of the heart to contract in synchrony to result in efficient pumping functions indicated by a normal hemodynamic performance. A blocked or otherwise abnormal electrical conduction and/or deteriorated myocardial tissue cause dyssynchronous contraction of the heart, resulting in poor hemodynamic performance including a diminished blood supply to the heart and the rest of the body. The condition where the heart fails to pump enough blood to meet the body's metabolic needs is known as heart failure.

Myocardial infarction (MI) is the necrosis of portions of the myocardial tissue resulted from cardiac ischemia, a condition in which the myocardium is deprived of adequate oxygen and metabolite removal due to an interruption in blood supply caused by an occlusion of a blood vessel such as a coronary artery. The necrotic tissue, known as infarcted tissue, loses the contractile properties of the normal, healthy myocardial tissue. Consequently, the overall contractility of the myocardium is weakened, resulting in an impaired hemodynamic performance. Following an MI, cardiac remodeling starts with expansion of the region of infarcted tissue and progresses to a chronic, global expansion in the size and change in the shape of the entire left ventricle. The consequences include a further impaired hemodynamic performance and a significantly increased risk of developing heart failure, as well as a risk of suffering recurrent MI.

Cardiac stimulation therapies have been applied to restore functions of the electrical conduction system and reduce the deterioration of myocardial tissue by delivering electrical pulses to the heart. Their potential benefits to a patient are achieved or maximized when such therapies are adaptive to the patient's cardiac condition and other physiological factors influencing the hemodynamic performance, which change over time. A cardiac stimulation therapy may also have unintended effects on the hemodynamic performance or cardiac remodeling, with the degree of impact dependent on the patient's cardiac condition and metabolic need. In one example, transiently delivering pacing pulses at a relatively high rate may provide a level of hemodynamic performance that satisfies the patient's instantaneous metabolic need for participating in an intense physical activity. However, delivering pacing pulses at a relatively high rate on a chronic basis may result in further deterioration of myocardial tissue. In another example, a cardiac stimulation therapy preventing further deterioration of myocardial tissue may significantly limit the patient's exercise capacity because the hemodynamic performance is further impaired when therapy is being delivered.

For these and other reasons, there is a need to modulate the delivery of cardiac stimulation therapies based on the patient's cardiac conditions and/or other physiological factors influencing the hemodynamic performance.

SUMMARY

A CRM system includes a non-invasive hemodynamic sensing device and an implantable medical device to sense a hemodynamic signal and derive one or more cardiac performance parameters from the hemodynamic signal. The non-invasive hemodynamic sensing device includes at least a portion configured for external attachment to a body in which the implantable medical device is implanted. The one or more cardiac performance parameters are used for various diagnostic, monitoring, and therapy control purposes.

In one embodiment, a system includes a non-invasive hemodynamic sensing device and an implantable medical device. The non-invasive hemodynamic sensing device is to be attached to an external appendage of a body and includes a hemodynamic sensor, a sensor signal processor, and a sensor telemetry circuit. The hemodynamic sensor senses a hemodynamic signal. The sensor signal processor produces hemodynamic data associated with the hemodynamic signal. The sensor telemetry circuit transmits the hemodynamic data from the non-invasive hemodynamic sensing device to the implantable medical device. The implantable medical device includes an implant telemetry circuit, an electrical stimulation circuit, and a stimulation controller. The implant telemetry circuit receives the hemodynamic data from the non-invasive hemodynamic sensing device. The electrical stimulation circuit delivers electrical stimulation to the body. The stimulation controller controls the delivery of the electrical stimulation using one or more stimulation parameters and includes a stimulation parameter adjustment module. The stimulation parameter adjustment module adjusts the one or more stimulation parameters using the hemodynamic data.

In one embodiment, a method for delivering electrical stimulation is provided. A hemodynamic signal is sensed using a non-invasive hemodynamic sensor attached to an external appendage of a body. Hemodynamic data associated with the hemodynamic signal are produced and transmitted to an implantable medical device through a wireless communication link. One or more stimulation parameters are adjusted using the hemodynamic data using a stimulation controller of the implantable medical device. The delivery of the electrical stimulation is controlled using the one or more stimulation parameters. The electrical stimulation is delivered from the implantable medical device.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof. The scope of the present invention is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

This document discusses a cardiac rhythm management (CRM) system that senses a hemodynamic signal using a non-invasive hemodynamic sensing device configured for attachment to an appendage of a body of a patient. The non-invasive hemodynamic sensing device is attached to the body of the patent without the need of incision into the body or removal of biological tissue from the body. Once attached to the body, the non-invasive hemodynamic sensing device transmits the sensed hemodynamic signal to an implantable medical device for therapeutic and/or diagnostic uses. In various embodiments, the non-invasive hemodynamic sensing device includes a hemodynamic sensor such as a plethysmography sensor or an oximeter to sense a hemodynamic signal indicative of arterial blood volume, pulse pressure, blood oxygen saturation, and/or heart rate. In various embodiments, one or more cardiac performance parameters are derived from the hemodynamic signal and used to adjust or optimize cardiac and/or neural stimulation therapies, detect arrhythmias, and/or monitor cardiac performance. In various embodiments, the CRM system of the present subject matter allows frequent diagnoses of the patient's cardiac functions and adjustments of therapies in response to changes in the patient's cardiac functions without frequent visits to a physician's office or other healthcare facilities. For example, the patient may be instructed to attach the non-invasive hemodynamic sensing device periodically to allow for periodic optimization of therapy parameters by the implantable medical device using the hemodynamic signal. The non-invasive sensing of the hemodynamic signal provides for simplicity and low power consumption for the implantable medical device.

Figure 1:
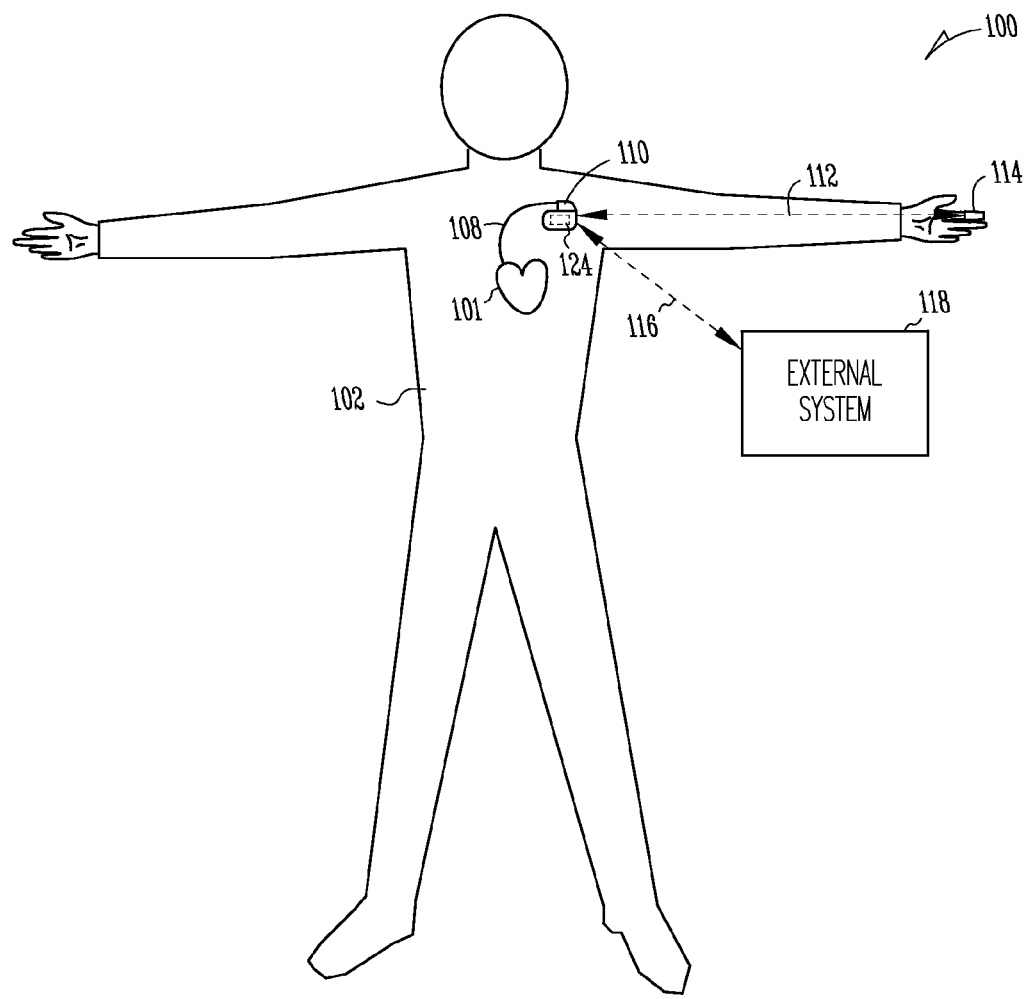
FIG. 1 is an illustration of an embodiment of a CRM system and portions of an environment in which the CRM system is used.

FIG. 1 is an illustration of an embodiment of a CRM system 100 and portions of an environment in which system 100 is used. System 100 includes a non-invasive hemodynamic sensing device 114, an implantable medical device 110, a lead system 108, an external system 118, a telemetry link 112 providing for communication between non-invasive hemodynamic sensing device 114 and implantable medical device 110, and another telemetry link 116 providing for communication between implantable medical device 110 and external system 118.

Non-invasive hemodynamic sensing device 114 includes a hemodynamic sensor that senses a hemodynamic signal. In various embodiments, the hemodynamic signal is indicative of one or more of arterial blood volume, pulse pressure, blood oxygen saturation, and heart rate. At least a portion of non-invasive hemodynamic sensing device 114 is configured for attachment to an external body appendage. In one embodiment, as illustrated in FIG. 1, non-invasive hemodynamic sensing device 114 is a finger clip sensor. In another embodiment, at least a portion of non-invasive hemodynamic sensing device 114 is a clip sensor configured for attachment to a toe or an ear. In another embodiment, at least a portion of non-invasive hemodynamic sensing device 114 is a cuff sensor configured for attachment to an arm or wrist. In one embodiment, non-invasive hemodynamic sensing device 114 includes a plethysmography sensor that senses arterial blood volume over time, from which peripheral pulse pressure and heart rate can be determined. In another embodiment, non-invasive hemodynamic sensing device 114 includes a pulse oximeter that senses blood oxygen saturation. In another embodiment, non-invasive hemodynamic sensing device 114 includes a cuff pressure sensor that senses peripheral blood pressures including systolic and diastolic pressures, from which a pulse pressure can be calculated. Non-invasive hemodynamic sensing device 114 processes the sensed hemodynamic signal to produce hemodynamic data and transmits the hemodynamic data to implantable medical device 110. The hemodynamic data include data representative of the sensed hemodynamic signal and/or one or more cardiac performance parameters derived from the sensed hemodynamic signal.

In various embodiments, implantable medical device 110 is an implantable CRM device including one or more of a pacemaker, a cardioverter/defibrillator, a cardiac resynchronization therapy (CRT) device, a cardiac remodeling control therapy (RCT) device, a neural stimulator, a drug delivery device or a drug delivery controller, a biological therapy device, and a physiological monitoring device. As illustrated in FIG. 1, implantable medical device 110 is implanted in a body 102. In various embodiments, lead system 108 includes leads for sensing physiological signals and delivering pacing pulses, cardioversion/defibrillation shocks, neural stimulation pulses, pharmaceutical agents, biological agents, and/or other types of energy or substance for treating cardiac disorders. In one embodiment, lead system 108 includes one or more pacing-sensing leads each including at least one electrode placed in or on a heart 101 for sensing electrogram and/or delivering pacing pulses. In other embodiments, electrodes placed in body 102 but away from heart 101 are used to sense physiological signals and deliver pacing pulses, cardioversion/defibrillation shocks, neural stimulation pulses, pharmaceutical agents, biological agents, and/or other types of energy or substance for treating cardiac disorders.

Implantable medical device 110 includes an implant controller 124 that receives the hemodynamic data from non-invasive hemodynamic sensing device 114 and uses the hemodynamic data for diagnostic and/or therapy control purposes. In one embodiment, non-invasive hemodynamic sensing device 114 produces the one or more cardiac performance parameters and transmits data representative of the one or more cardiac performance parameters to implantable medical device 110. In another embodiment, implantable medical device 110 produces the one or more cardiac performance parameters using the data representative of the sensed hemodynamic signal transmitted from non-invasive hemodynamic sensing device 114. In a further embodiment, implantable medical device 110 transmits data representative of the sensed hemodynamic signal and/or the one or more cardiac performance parameters to external system 118.

Telemetry link 112 is a wireless communication link that provides for communication between non-invasive hemodynamic sensing device 114 and implantable medical device 110. In one embodiment, telemetry link 112 is a radio-frequency (RF) electromagnetic telemetry link. In another embodiment, telemetry link 112 is a conductive link that uses body 102 as the conducting medium. In a specific embodiment, telemetry link 112 is an ultrasonic telemetry link. An example of an ultrasonic telemetry system is discussed in U.S. patent application Ser. No. 10/888,956, entitled "METHOD AND APPARATUS OF ACOUSTIC COMMUNICATION FOR IMPLANTABLE MEDICAL DEVICE," filed on Jul. 9, 2004, now issued as U.S. Pat. No. 7,489,967, assigned to Cardiac Pacemakers, Inc., which is incorporated herein by reference in its entirety. In another embodiment, non-invasive hemodynamic sensing device 114 communicates with implantable medical device 110 via external system 118. That is, external system 118 communicates with non-invasive hemodynamic sensing device 114 through a wired or wireless communication link and functions as a repeater.

External system 118 allows a user such as the physician or other caregiver to control the operation of implantable medical device 110 and obtain information acquired by implantable medical device 110, including the data representative of the sensed hemodynamic signal and/or the one or more cardiac performance parameters. In one embodiment, external system 118 includes a programmer communicating with implantable medical device 110 bi-directionally via telemetry link 116. In another embodiment, external system 118 is a patient management system including an external device communicating with a remote device through a telecommunication network. The external device is within the vicinity of implantable medical device 110 and communicates with implantable medical device 110 bi-directionally via telemetry link 116. The remote device allows the user to monitor and treat a patient from a distant location. The patient monitoring system is further discussed below, with reference to FIG. 9.

Telemetry link 116 is a wireless communication link that provides for communication between implantable medical device 110 and external system 118. The communication includes data transmission from implantable medical device 110 to external system 118. This includes, for example, transmitting real-time physiological data acquired by implantable medical device 110, extracting physiological data acquired by and stored in implantable medical device 110, extracting therapy history data stored in implantable medical device 110, and extracting data indicating an operational status of implantable medical device 110 (e.g., battery status and lead impedance). Telemetry link 116 also provides for data transmission from external system 118 to implantable medical device 110. This includes, for example, programming implantable medical device 110 to acquire physiological data, programming implantable medical device 110 to perform at least one self-diagnostic test (such as for a device operational status), and programming implantable medical device 110 to deliver at least one therapy. In one embodiment, telemetry link 116 is an inductive telemetry link. In one embodiment, telemetry link 116 is an RF electromagnetic telemetry link. In another embodiment, telemetry link 116 is an ultrasonic telemetry link.

Figure 2:
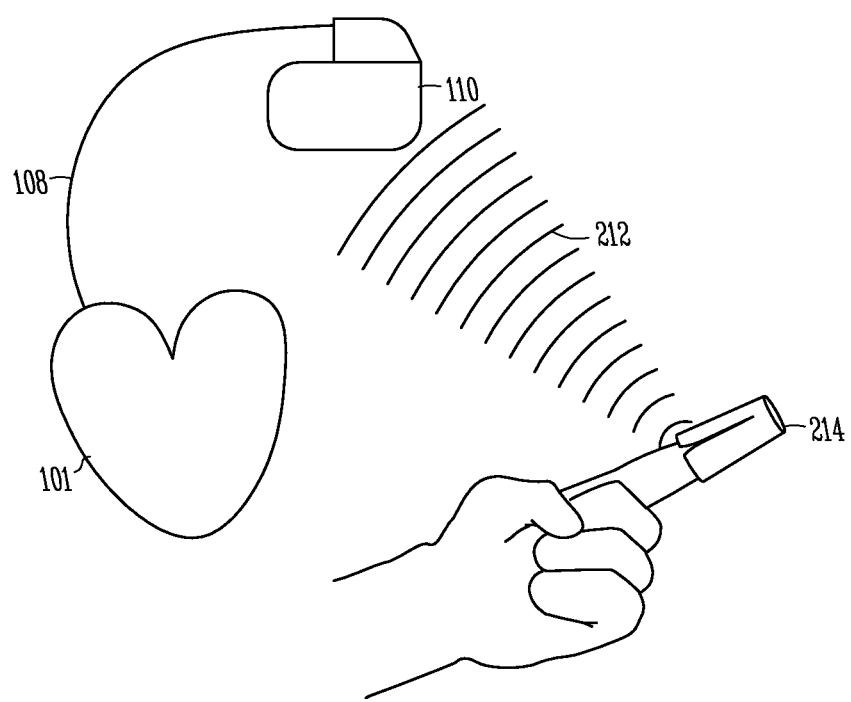
FIG. 2 is an illustration of an embodiment of a non-invasive hemodynamic sensing device of the CRM system.

FIG. 2 is an illustration of an embodiment of a non-invasive hemodynamic sensing device 214, which is a specific embodiment of non-invasive hemodynamic sensing device 114. Non-invasive hemodynamic sensing device 214 includes a finger clip device that includes a hemodynamic sensor, a sensor signal processor, a sensor telemetry circuit, and a battery. A telemetry link 212, which is a specific embodiment of telemetry link 112, provides for communication between non-invasive hemodynamic sensing device 214 and implantable medical device 110.

Figure 3:
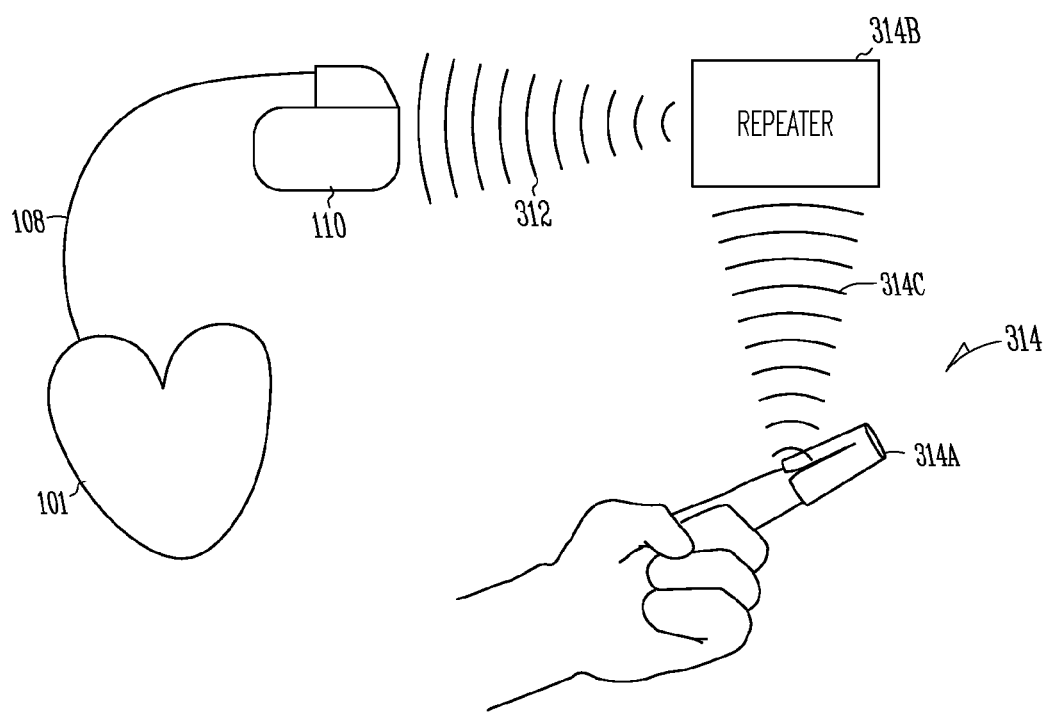
FIG. 3 is an illustration of another embodiment of the non-invasive hemodynamic sensing device of the CRM system.

FIG. 3 is an illustration of an embodiment of a non-invasive hemodynamic sensing device 314, which is a specific embodiment of non-invasive hemodynamic sensing device 114. Non-invasive hemodynamic sensing device 314 includes a sensor 314A and a repeater 314B. Sensor 314A is a finger clip device that includes a hemodynamic sensor, a signal processor, and a battery. Repeater 314B is a portable device that includes another signal processor, a sensor telemetry circuit for communicating with implantable medical device 110, and another battery. In one embodiment, as illustrated in FIG. 3, a telemetry link 314C provides for wireless communication between sensor 314A and repeater 314B. In an alternative embodiment, sensor 314A and repeater 314B are electrically connected using a cable, eliminating the need for telemetry link 314C and the battery in the finger clip device. A telemetry link 312, which is a specific embodiment of telemetry link 112, provides for communication between repeater 314B and implantable medical device 110.

Figure 4:
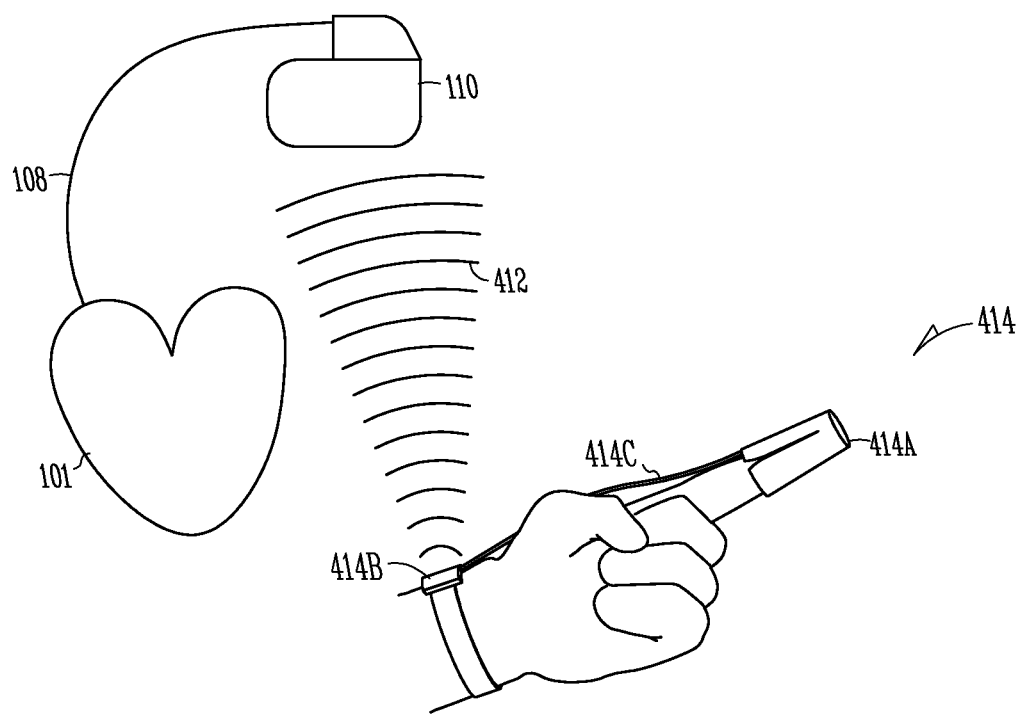
FIG. 4 is an illustration of another embodiment of the non-invasive hemodynamic sensing device of the CRM system.

FIG. 4 is an illustration of an embodiment of a non-invasive hemodynamic sensing device 414, which is a specific embodiment of non-invasive hemodynamic sensing device 114. Non-invasive hemodynamic sensing device 414 includes a sensor 414A electrically connected to a repeater 414B using a cable 414C. Sensor 414A is a finger clip device that includes a hemodynamic sensor. Repeater 414B is a portable device that includes a signal processor, a sensor telemetry circuit, and a battery. In one embodiment, as illustrated in FIG. 4, repeater 414B is incorporated into a wrist band. A telemetry link 412, which is a specific embodiment of telemetry link 112, provides for communication between repeater 414B and implantable medical device 110.

Various specific embodiments of non-invasive hemodynamic sensing device 114 are illustrated in FIGS. 2-4 for illustrative but not restrictive purposes. In various specific embodiments, non-invasive hemodynamic sensing device 114 includes a hemodynamic sensor that is incorporated into a clip device that can be attached on to a body appendage such as a finger, a toe, or an ear or a cuff device that can be attached around a portion of a body appendage such as a limb. In various specific embodiments, non-invasive hemodynamic sensing device 114 includes a hemodynamic sensor, a signal processor, a sensor telemetry circuit, and a battery. These components are distributed in one or more device units based on design and user acceptability considerations.

Figure 5:
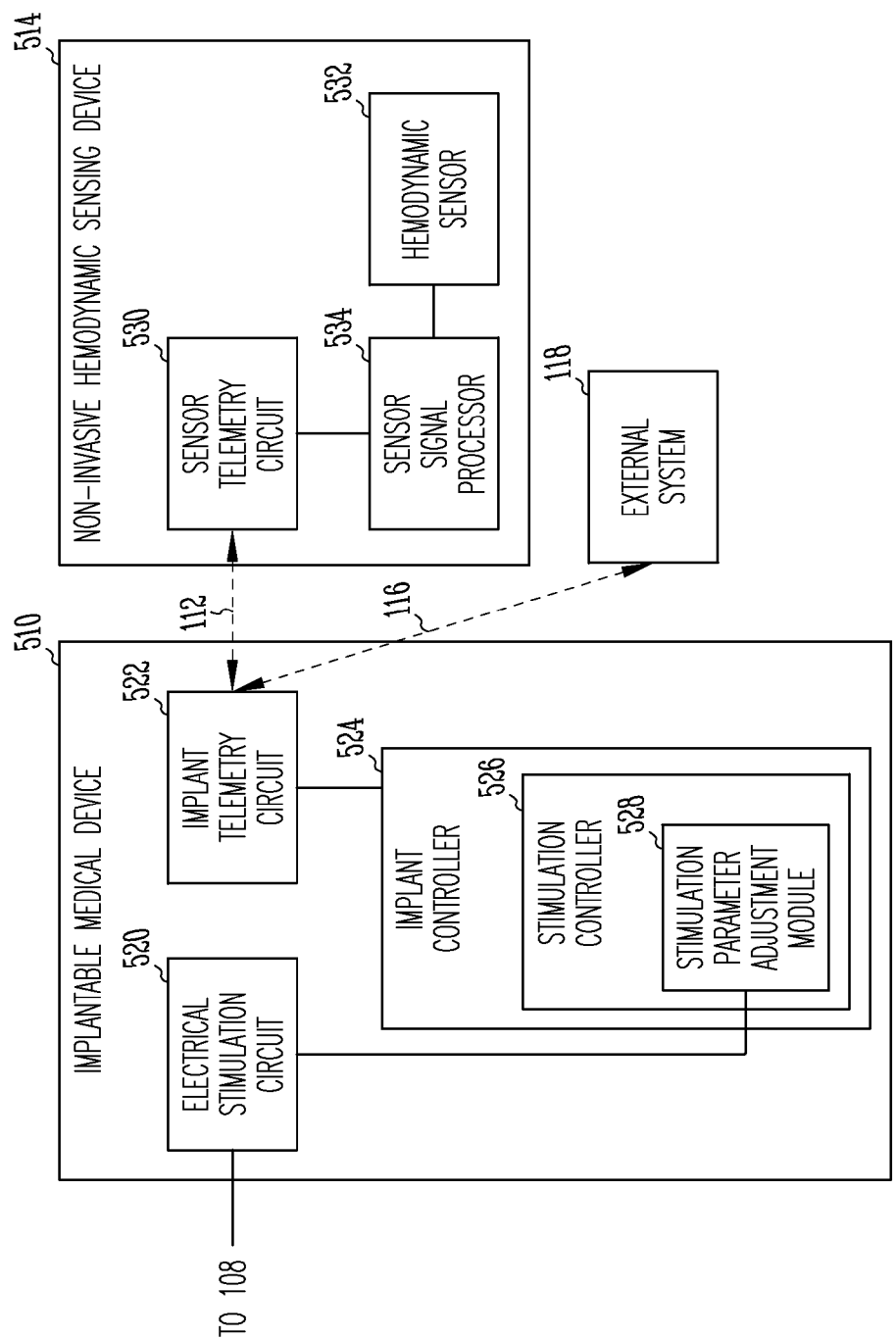
FIG. 5 is a block diagram illustrating an embodiment of portions of a circuit of the CRM system.

FIG. 5 is a block diagram illustrating an embodiment of portions of a circuit of CRM system 100, including a non-invasive hemodynamic sensing device 514, an implantable medical device 510, and external system 118. Non-invasive hemodynamic sensing device 514 is a specific embodiment of non-invasive hemodynamic sensing device 114 and includes a hemodynamic sensor 532, a sensor signal processor 534, and a sensor telemetry circuit 530. Hemodynamic sensor 532 is configured for attachment to an external appendage of body 102 to sense a hemodynamic signal. Sensor signal processor 534 produces hemodynamic data associated with the hemodynamic signal. Sensor telemetry circuit 530 transmits the hemodynamic data from non-invasive hemodynamic sensing device 514 to implantable medical device 510 via telemetry link 112. Implantable medical device 510 includes an implant telemetry circuit 522, an electrical stimulation circuit 520, and an implant controller 524. Implant telemetry circuit 522 receives the hemodynamic data from non-invasive hemodynamic sensing device 514 via telemetry link 112. Electrical stimulation circuit 520 delivers electrical stimulation pulses to heart 101 and/or other portions of body 102. Examples of such electrical stimulation pulses include pacing pulses, cardioversion/defibrillation pulses, and neural stimulation pulses. Implant controller 524 is a specific embodiment of implant controller 124 and includes a stimulation controller 526. Stimulation controller 526 controls the delivery of the electrical stimulation pulses using one or more stimulation parameters and includes a stimulation parameter adjustment module 528 that adjusts the one or more stimulation parameters using the hemodynamic data.

In one embodiment, hemodynamic sensor 532 is incorporated into a finger clip device such as one of those illustrated in FIG. 1. In other embodiments, hemodynamic sensor 532 is incorporated into a toe clip device or an ear clip device. In one embodiment, hemodynamic sensor 532 is a plethysmography sensor that senses arterial blood volume over time, from which peripheral pulse pressure and heart rate can be determined. In another embodiment, hemodynamic sensor 532 is a pulse oximeter that senses blood oxygen saturation.

Figure 6:
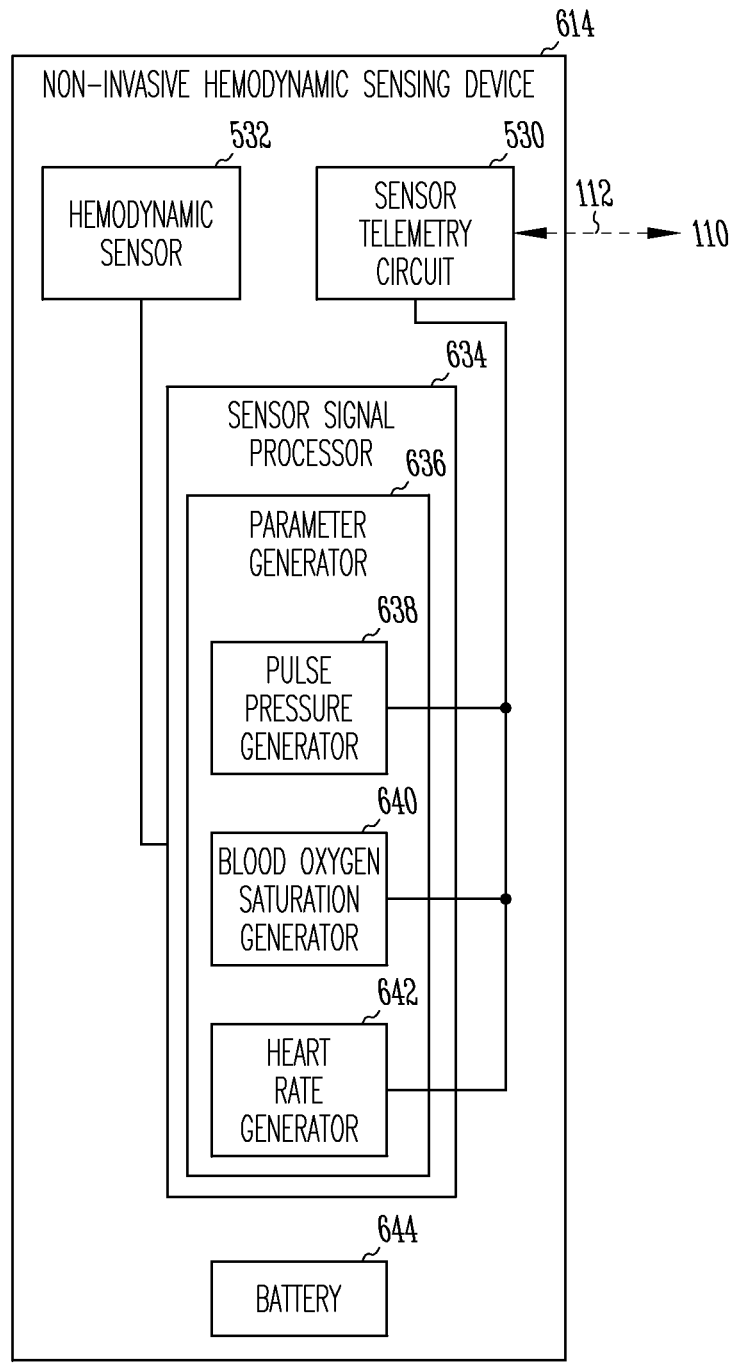
FIG. 6 is a block diagram illustrating an embodiment of portions of a circuit of a non-invasive hemodynamic sensor of the CRM system.

FIG. 6 is a block diagram illustrating an embodiment of portions of a circuit of a non-invasive hemodynamic sensing device 614, which is a specific embodiment of non-invasive hemodynamic sensing device 114. Non-invasive hemodynamic sensing device 614 includes hemodynamic sensor 532, sensor telemetry circuit 530, a sensor signal processor 634, and a battery 644.

Sensor signal processor 634 produces hemodynamic data associated with the hemodynamic signal. The hemodynamic data include data representative of the hemodynamic signal and/or data representative of one or more cardiac performance parameters derived from the hemodynamic signal. The one or more cardiac performance parameters are each being a measure of cardiac function. In one embodiment, as illustrated in FIG. 6, sensor signal processor 634 includes a parameter generator 636 that produces the one or more cardiac performance parameters from the hemodynamic signal. Parameter generator 636 includes a pulse pressure generator 638, a blood oxygen saturation generator 640, and a heart rate generator 642. Pulse pressure generator 638 produces a pulse pressure parameter representative of pulse pressure using the hemodynamic signal. Blood oxygen saturation generator 640 produces a blood oxygen saturation parameter representative of blood oxygen saturation using the hemodynamic signal. Heart rate generator 642 produces a heart rate parameter representative of the heart rate using the hemodynamic signal. In various embodiments, depending on the specific diagnostic and/or therapeutic needs, parameter generator 636 includes any one or more of pulse pressure generator 638, blood oxygen saturation generator 640, and heart rate generator 642. In an alternative embodiment, implantable medical device 110 receives the data representative of the hemodynamic signal and performs the functions of parameter generator 636.

Battery 644 provides non-invasive hemodynamic sensing device 614 with energy for its operation. In one embodiment, battery 644 is a rechargeable battery. In a specific embodiment, non-invasive hemodynamic sensing device 614 is used intermittently, such as on a periodic basis. A battery charger is provided for charging battery 644 when non-invasive hemodynamic sensing device 614 is not in use.

Figure 7:
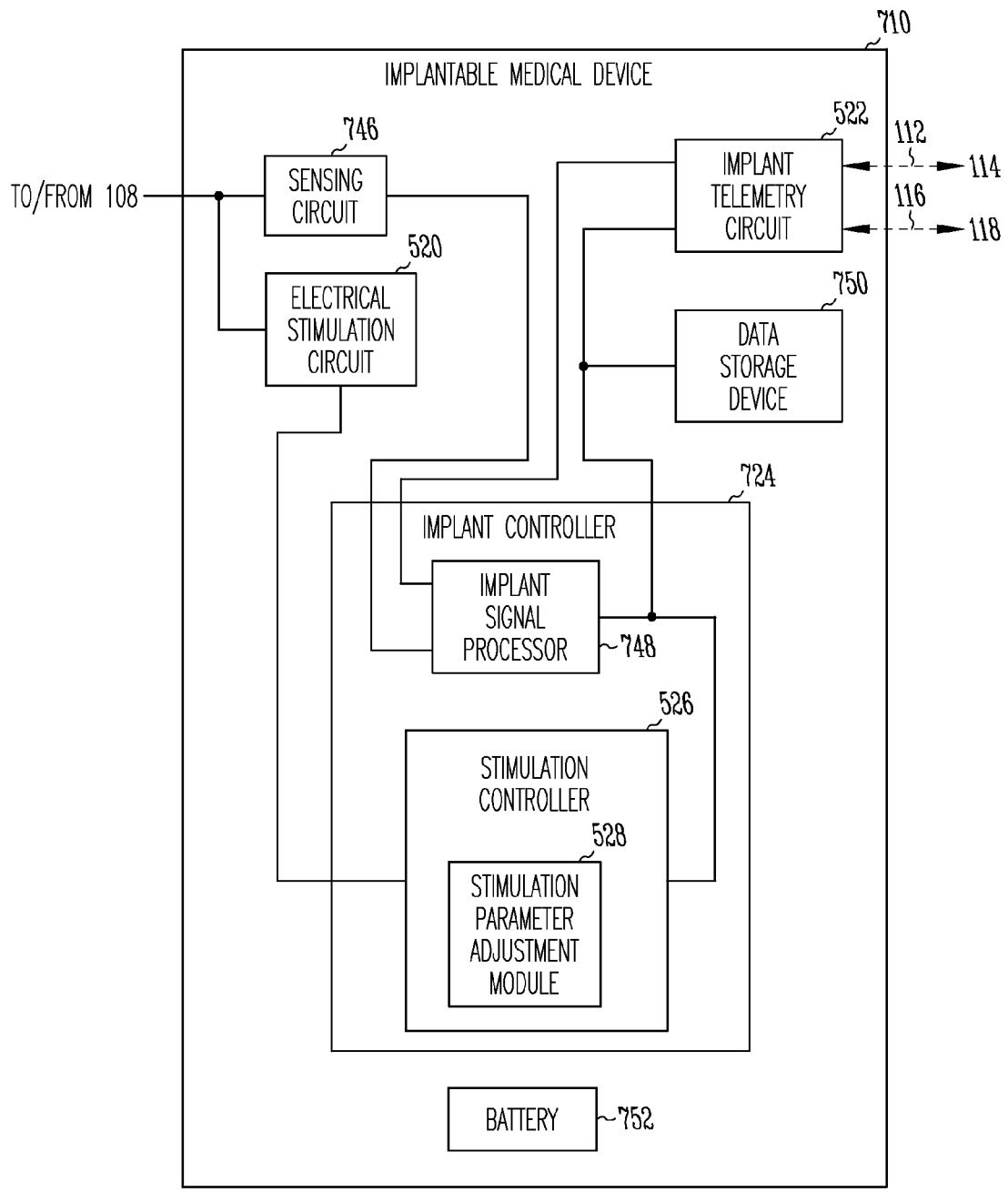
FIG. 7 is a block diagram illustrating an embodiment of portions of a circuit of an implantable medical device of the CRM system.

FIG. 7 is a block diagram illustrating an embodiment of portions of a circuit of an implantable medical device 710, which is a specific embodiment of implantable medical device 110. Implantable medical device 710 includes a sensing circuit 746, electrical stimulation circuit 520, implant telemetry circuit 522, a data storage device 750, an implant controller 724, and a battery 752.

Sensing circuit 746 senses one or more cardiac signals and/or other physiological signals. In various embodiments, the sensed signals are used for control of delivery of electrical stimulation pulses by electrical stimulation circuit 520 and/or for monitoring cardiac functions.

Data storage device 750 stores various data including hemodynamic data received from non-invasive hemodynamic sensing device 114 and/or processed by implant controller 724. The data are stored for use by implant controller 724 to control therapy deliveries and/or for transmission to external system 118 upon request.

Implant controller 724 includes an implant signal processor 748 and stimulation controller 526. Implant signal processor 748 processes the signals sensed by sensing circuit 746. In one embodiment, in which non-invasive hemodynamic sensing device 114 produces the data representative of the hemodynamic signal but does not produce the one or more cardiac performance parameters using the hemodynamic signal, implant signal processor 748 (instead of sensor signal processor 634) includes parameter generator 636, which produces the one or more cardiac performance parameters using the data representative of the hemodynamic signal. Stimulation controller 526 controls the delivery of the electrical stimulation pulses from electrical stimulation circuit 520 using selected signals processed and parameters produced by implant signal processor 748.

Battery 752 provides implantable medical device 710 with the energy for its operation. The longevity of implantable medical device 710 depends on the power consumption of the device and the life of battery 752.

Figure 8:
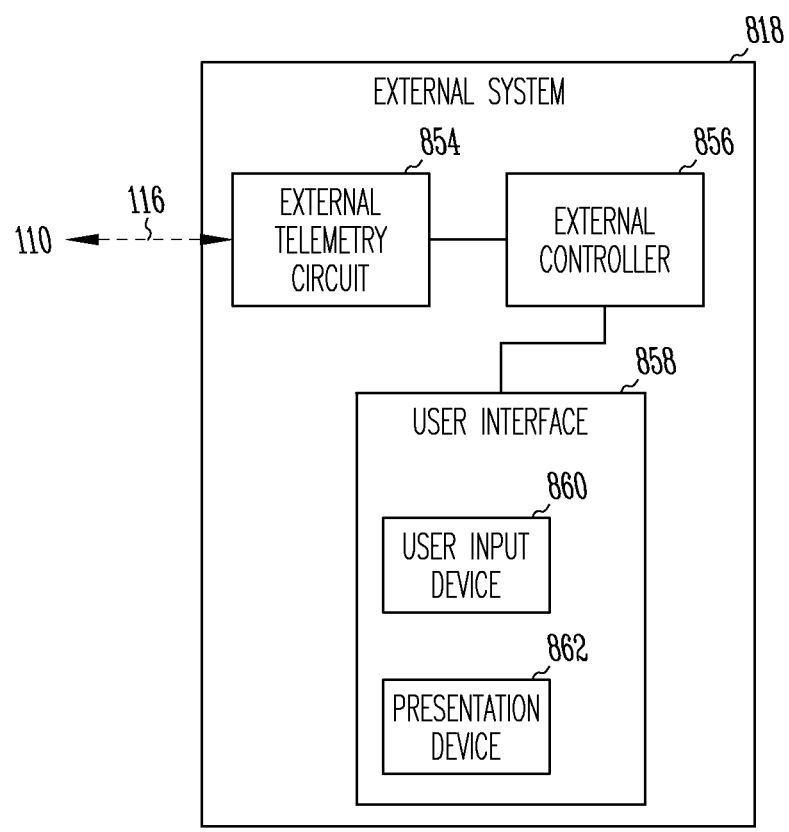
FIG. 8 is a block diagram illustrating an embodiment of portions of a circuit of an external system of the CRM system.

FIG. 8 is a block diagram illustrating an embodiment of portions of a circuit of an external system 818, which is a specific embodiment of external system 118. External system 818 includes an external telemetry circuit 854, an external controller 856, and a user interface 858. External telemetry circuit 818 transmits data to, and receives data from, implantable medical device 110 via telemetry link 116. External controller 856 controls the operation of external device 818, including the processing of information acquired by and transmitted from implantable medical device 110. User interface 858 includes a user input device 860 and a presentation device 862. User input device 858 receive user commands from the physician or other caregiver and/or the patient. The user commands include a data retrieval command for retrieving data selected from the data stored in data storage device 750, including data associated with the hemodynamic signal sensed by non-invasive hemodynamic sensing device 114. Presentation device 862 presents various diagnostic and therapeutic information, including the hemodynamic signal and/or the one or more cardiac performance parameters derived from the hemodynamic signal.

In one embodiment, external system 818 includes a programmer. In another embodiment, external system 818 includes a handheld device for use by the patient and/or the physician or other caregiver. In another embodiment, external system 818 includes a patient management system such as described below with reference to FIG. 9.

Figure 9:
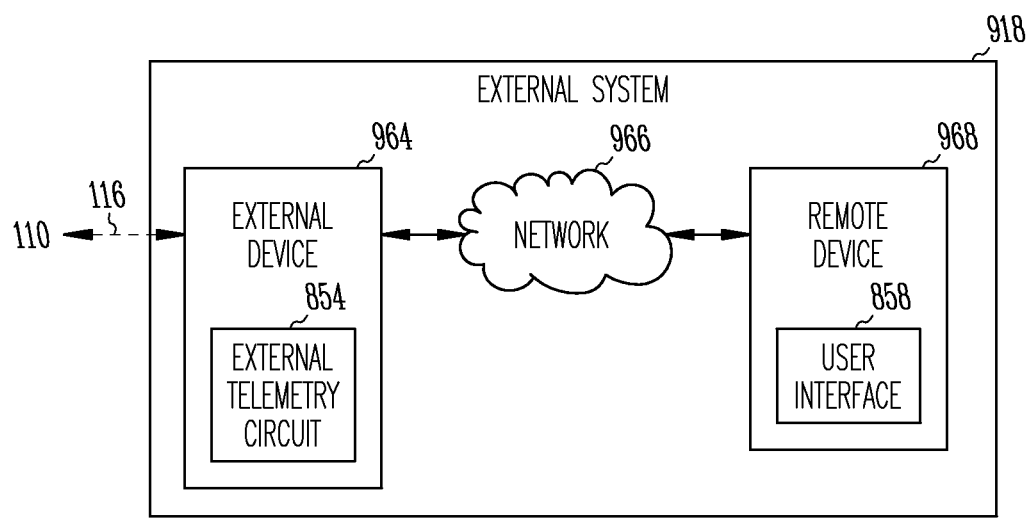
FIG. 9 is a block diagram illustrating an embodiment of the external system.

FIG. 9 is a block diagram illustrating an embodiment of an external system 918. External system 918 represents a special embodiment of external system 118 in which CRM system 100 includes an external patient management system. As illustrated in FIG. 9, external system 918 includes an external device 964, a telecommunication network 966, and a remote device 968. External device 964 is placed within the vicinity of implantable medical device 110 and includes external telemetry circuit 854 to communicate with implantable medical device 110 via telemetry link 116. Remote device 968 is in one or more remote locations and communicates with external device 964 through network 966, thus allowing the physician or other caregiver to monitor and treat the patient from a distant location and/or allowing access to various treatment resources from the one or more remote locations. In one embodiment, network 966 is the Internet. In one embodiment, remote device 968 includes user interface 858 to allow the physician or other caregiver to monitor the patient and/or to start, stop, or adjust a therapy in a location remote from the patient.

Figure 10:
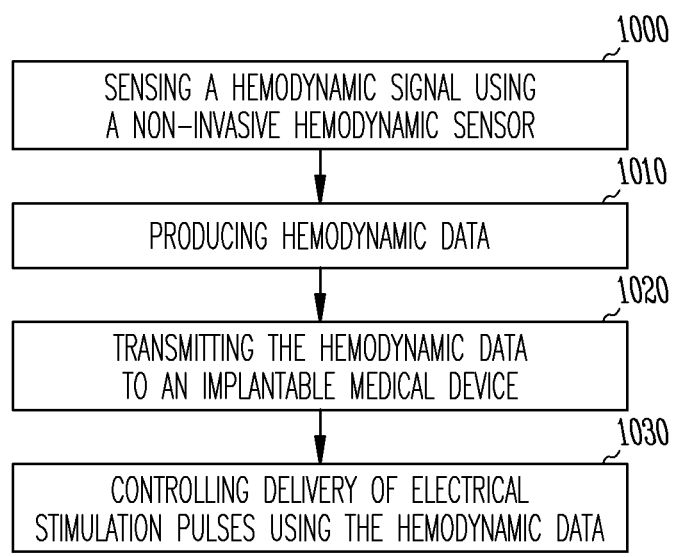
FIG. 10 is a flow chart illustrating a method for operating a CRM system including a non-invasive hemodynamic sensing device and an implantable medical device.

FIG. 10 is a flow chart illustrating a method for operating a CRM system including a non-invasive hemodynamic sensor and an implantable medical device. One example of such a CRM system is CRM system 100.

A hemodynamic signal is sensed using a non-invasive hemodynamic sensor at 1000. The hemodynamic signal indicates one or more of arterial blood volume, pulse pressure, and oxygen saturation of blood. The pulse pressure, in turn, indicates changes in cardiac output. In one embodiment, the hemodynamic signal includes a plethysmogram. The plethysmogram is sensed by using light to sense changes in arterial blood volume over time. Peripheral pulse pressure and heart rate are determined using the changes in arterial blood volume. In another embodiment, the hemodynamic signal includes an oximetry signal. The oximetry signal is sensed by using light to sense blood oxygen saturation.

Hemodynamic data associated with the hemodynamic signal are produced at 1010. In one embodiment, the hemodynamic data include data representative of the sensed hemodynamic signal. The non-invasive hemodynamic sensor produces the data representative of the sensed hemodynamic signal (that are later used by the implantable medical device to produce one or more cardiac performance parameters). In another embodiment, the hemodynamic data include data representative of the sensed hemodynamic signal and/or data representative of one or more cardiac performance parameters. The non-invasive hemodynamic sensor produces the one or more cardiac performance parameters using the sensed hemodynamic signal and produces data representative of the sensed hemodynamic signal and/or data representative of the one or more cardiac performance parameters. The one or more cardiac performance parameters are each a measure of cardiac function. Examples of such cardiac performance parameters from the hemodynamic signal include a pulse pressure parameter representative of the pulse pressure, a blood oxygen saturation parameter representative of the blood oxygen saturation, and a heart rate parameter representative of the heart rate.

The hemodynamic data are transmitted to the implantable medical device at 1020. In one embodiment, the hemodynamic data are transmitted to the implantable medical device using RF electromagnetic telemetry. In another embodiment, the hemodynamic data are transmitted to the implantable medical device using ultrasonic telemetry.

Delivery of electrical stimulation pulses is controlled using the hemodynamic data at 1030. The delivery of electrical stimulation pulses is controlled using one or more stimulation parameters. The one or more stimulation parameters are adjusted using the one or more cardiac performance parameters. In one embodiment, at least one stimulation parameter of the one or more stimulation parameters is approximately optimized using the one or more cardiac performance parameters.

In one embodiment, steps 1000-1030 are performed according to a predetermined schedule, such as on a periodic basis. This allows adjustment or optimization of the delivery of the electrical stimulation pulses according to the patient's changing cardiac function and changing demand for hemodynamic performance. In one embodiment, steps 1000-1030 are performed when initiated by the physician or other caregiver following a diagnosis, when initiated automatically by the CRM system, and/or when initiated by the patient who perceives a need to do so.

Example 1

Post-MI Pacing Control

In one embodiment, CRM system 100 provides feedback control to a post-MI pacing therapy using cardiac performance as an input. The post-MI pacing therapy is delivered to a patient who has suffered MI to control ventricular remodeling by inducing ventricular pre-excitation, thus reducing myocardial loading during systole. An example of such a post-MI pacing therapy is discussed in U.S. Pat. No. 6,973,349, "METHOD AND APPARATUS FOR MINIMIZING POST-INFARCT VENTRICULAR REMODELING," assigned to Cardiac Pacemakers, Inc., which is incorporated herein by reference in its entirety. Such myocardial unloading prevents the myocardium from further deterioration but tend to compromise hemodynamic performance, especially when the patient is active. The feedback control is applied to balance the myocardial unloading with required cardiac output to ensure that the post-MI pacing therapy does not compromise the patient's cardiac performance to an intolerable degree.

Figure 11:
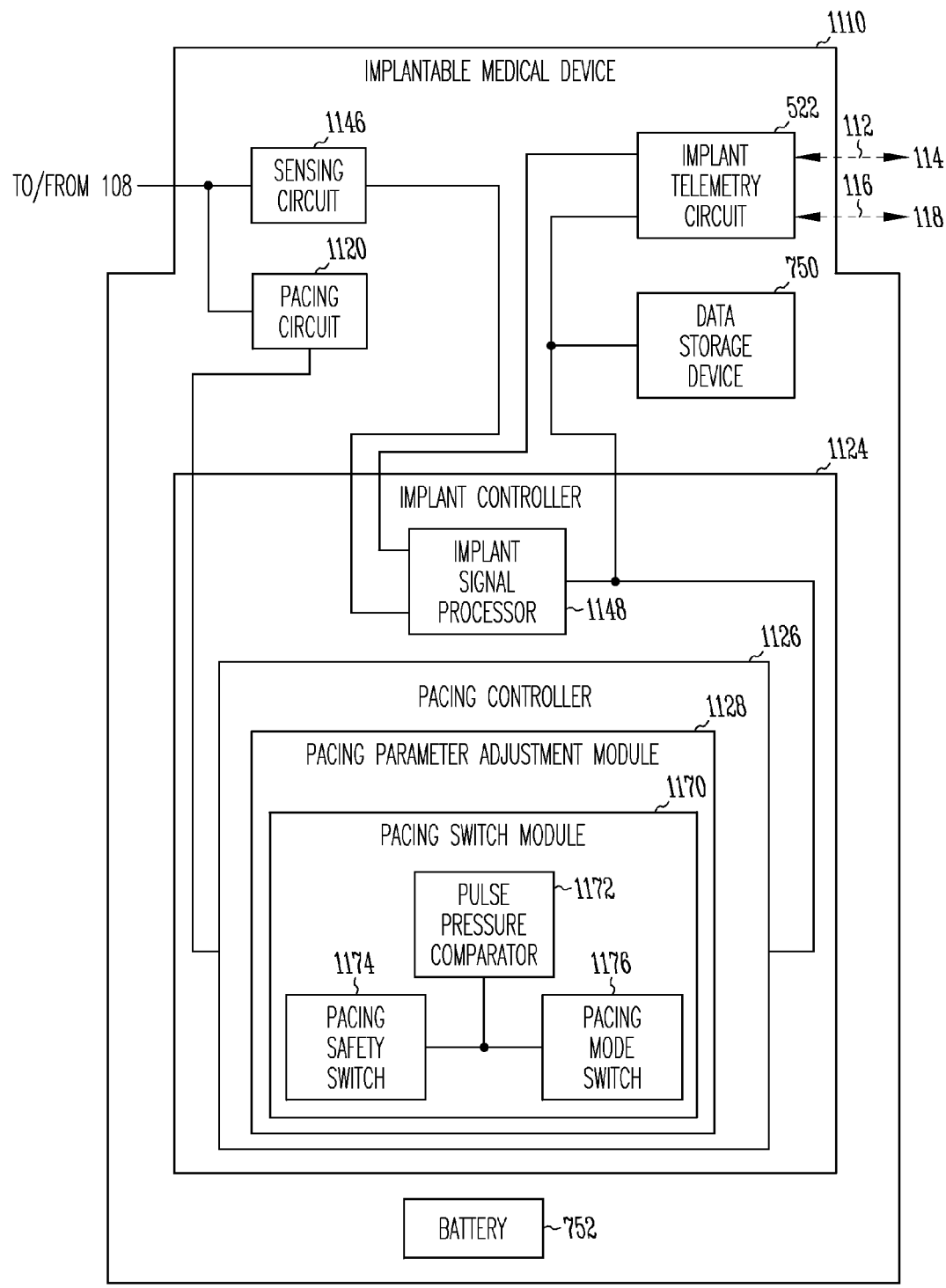
FIG. 11 is a block diagram illustrating an embodiment of portions of a circuit of an implantable medical device that controls post-MI pacing using a hemodynamic signal sensed by a non-invasive hemodynamic sensor.

FIG. 11 is a block diagram illustrating an embodiment of portions of a circuit of an implantable medical device 1110, which is a specific embodiment of implantable medical device 110. Implantable medical device 1110 delivers a post-MI pacing therapy and provides feedback control for that therapy using the hemodynamic data transmitted from non-invasive hemodynamic sensing device 114. Implantable medical device 1110 includes a sensing circuit 1146, a pacing circuit 1120, implant telemetry circuit 522, data storage device 750, implant controller 1124, and battery 752.

Sensing circuit 1146 is a specific embodiment of sensing circuit 746 and senses one or more electrograms for pacing control. Pacing circuit 1120 is a specific embodiment of electrical stimulation circuit 520 and delivers pacing pulses to heart 101 through lead system 108.

Implant controller 1124 includes an implant signal processor 1148 and a pacing controller 1126. Implant signal processor 1148 processes the one or more electrograms for use by pacing controller 1126 and provides pacing controller 1126 with one or more cardiac performance parameters that are received from non-invasive hemodynamic sensing device 114 or produced from the hemodynamic data received from non-invasive hemodynamic sensing device 114. Pacing controller 1126 controls the delivery of the pacing pulses using one or more pacing parameters and includes a pacing parameter adjustment module 1128. Pacing parameter adjustment module 1128 adjusts the one or more pacing parameters using the one or more cardiac performance parameters. In one embodiment, pacing parameter adjustment module 1128 adjusts the one or more pacing parameters to approximately maximize ventricular unloading while the patient's cardiac output, as indicated by the pulse pressure parameter, does not drop below an intolerable level.

In one embodiment, as illustrated in FIG. 11, pacing parameter adjustment module 1128 includes a pacing switch module 1170 that allows for starting, stopping, and adjustment of the delivery of pacing pulses using the pulse pressure parameter. Pacing switch module 1170 includes a pulse pressure comparator 1172, a pacing safety switch 1174, and a pacing mode switch 1176. In other embodiments, pacing parameter adjustment module 1128 includes any one or both of pacing safety switch 1174 and pacing mode switch 1176. Pulse pressure comparator 1172 compares the pulse pressure parameter to a predetermined threshold pulse pressure. The threshold pulse pressure is a pulse pressure level below which the patient's cardiac output is considered too low. In one embodiment, pacing safety switch 1174 stops the delivery of the pacing pulses when the pulse pressure parameter is below the predetermined threshold pulse pressure. In another embodiment, pacing safety switch 1174 stops the delivery of the pacing pulses when the pulse pressure parameter drops below a first predetermined threshold pulse pressure and starts the delivery of the pacing pulses when the pulse pressure parameter rises above a second predetermined threshold pulse pressure. The first predetermined threshold pulse pressure is lower than the second predetermined threshold pulse pressure. In one embodiment, pacing mode switch 1176 switches between a cardiac resynchronization therapy (CRT) mode and a remodeling control therapy (RCT) mode based on the pulse pressure parameter. The CRT mode maximizes synchrony of ventricular contractions by maximizing the pulse pressure. The RCT mode limits ventricular remodeling by providing ventricular unloading. Pacing mode switch 1176 switches between the RCT mode and the CRT mode by switching between a first set of pacing parameters and a second set of pacing parameters. In a specific embodiment, pacing mode switch 1176 switches between the RCT mode and the CRT mode by switching between AV delays, interventricular (IV) delays (also referred to as IV offsets and left ventricular offsets), and/or ventricular pacing sites. In a specific embodiment, pacing mode switch 1176 switches from the RCT mode to the CRT mode when the pulse pressure parameter is below the predetermined threshold pulse pressure. In another specific embodiment, pacing switch 1176 switches from the RCT mode to the CRT mode when the pulse pressure parameter is drops below a first predetermined threshold pulse pressure and switch from the CRT mode to the RCT mode when the pulse pressure parameter rises above a second predetermined threshold pulse pressure. The first predetermined threshold pulse pressure is lower than the second predetermined threshold pulse pressure.

Figure 12:
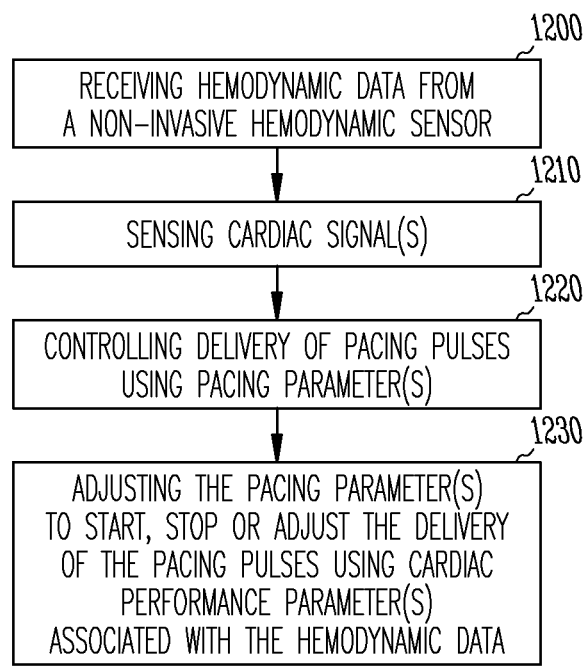
FIG. 12 is a flow chart illustrating a method for controlling post-MI pacing using a non-invasive hemodynamic sensing device and an implantable medical device.

FIG. 12 is a flow chart illustrating a method for controlling post-MI pacing using a non-invasive hemodynamic sensor and an implantable medical device. In one embodiment, the non-invasive hemodynamic sensor is non-invasive hemodynamic sensing device 114, including any of its specific embodiments, and the implantable medical device is implantable medical device 1110.

Hemodynamic data are received from the non-invasive hemodynamic sensor at 1200. In one embodiment, the hemodynamic data include data representative of one or more cardiac performance parameters. In another embodiment, the hemodynamic data include data representative of the sensed hemodynamic signal, and the implantable medical device produces the one or more cardiac performance parameters using the hemodynamic data. One or more cardiac signals such as electrograms are sensed at 1210 for pacing control. Delivery of pacing pulses is controlled using one or more pacing parameters at 1220. The one or more pacing parameters are adjusted to start, stop, or adjust the delivery of the pacing pulses using the hemodynamic data, including the one or more cardiac performance parameters, at 1230. In one embodiment, the one or more pacing parameters are adjusted to approximately maximize ventricular unloading while the pulse pressure parameter indicates that the patient's cardiac output is at a tolerable level.

In one embodiment of step 1230, the pulse pressure parameter is compared to a predetermined threshold pulse pressure for pacing safety control. In a specific embodiment, the delivery of the pacing pulses is stopped when the pulse pressure parameter is below the predetermined threshold pulse pressure. In another specific embodiment, the delivery of the pacing pulses is stopped when the pulse pressure parameter drops below a first predetermined threshold pulse pressure and started when the pulse pressure parameter rises above a second predetermined threshold pulse pressure. The first predetermined threshold pulse pressure is lower than the second predetermined threshold pulse pressure. In another embodiment of step 1230, the pulse pressure parameter is compared to a predetermined threshold pulse pressure for pacing mode control. The pacing mode is switched between a CRT mode and an RCT mode based on the pulse pressure parameter. The mode switching between the RCT mode and the CRT mode is accomplished by switching between a first set of pacing parameters and a second set of pacing parameters. In a specific embodiment, the mode switching between the RCT mode and the CRT mode is accomplished by switching between a first AV delay and a second AV delay. In a specific embodiment, the pacing mode is switched from the RCT mode to the CRT mode when the pulse pressure parameter is below the predetermined threshold pulse pressure. In another specific embodiment, the pacing mode is switched from the RCT mode to the CRT mode when the pulse pressure parameter drops below a first predetermined threshold pulse pressure and switched from the CRT mode to the RCT mode when the pulse pressure parameter rises above a second predetermined threshold pulse pressure. The first predetermined threshold cardiac output is lower than the second predetermined threshold pulse pressure.

In various embodiments, the hemodynamic data are used to control switching between therapy modes in response to the patient's need or condition indicated by the hemodynamic data. Examples of such therapy modes include two or more of a bradycardia pacing mode, a CRT mode, an RCT mode, a cardioversion mode, a defibrillation mode, and a neural stimulation mode.

Example 2

Neural Stimulation Control

In one embodiment, CRM system 100 provides heart rate and pulse pressure feedback control to a neural stimulation therapy that treats cardiovascular disorders. For example, neural stimulation pulses are delivered to the vagus nerve of a patient who has abnormally high blood pressure to lower the patient's blood pressure. The feedback control is applied to maintain the patient's blood pressure in a desirable range. In another example, neural stimulation pulses are delivered to the vagus nerve of a patient who has suffered MI to control post-MI ventricular remodeling. Such vagal stimulation is known to lower the patient's heart rate and pulse pressure. The feedback control is applied to balance the remodeling control with required cardiac output to ensure that the post-MI neural stimulation therapy does not compromise the patient's cardiac performance to an intolerable degree.

Figure 13:
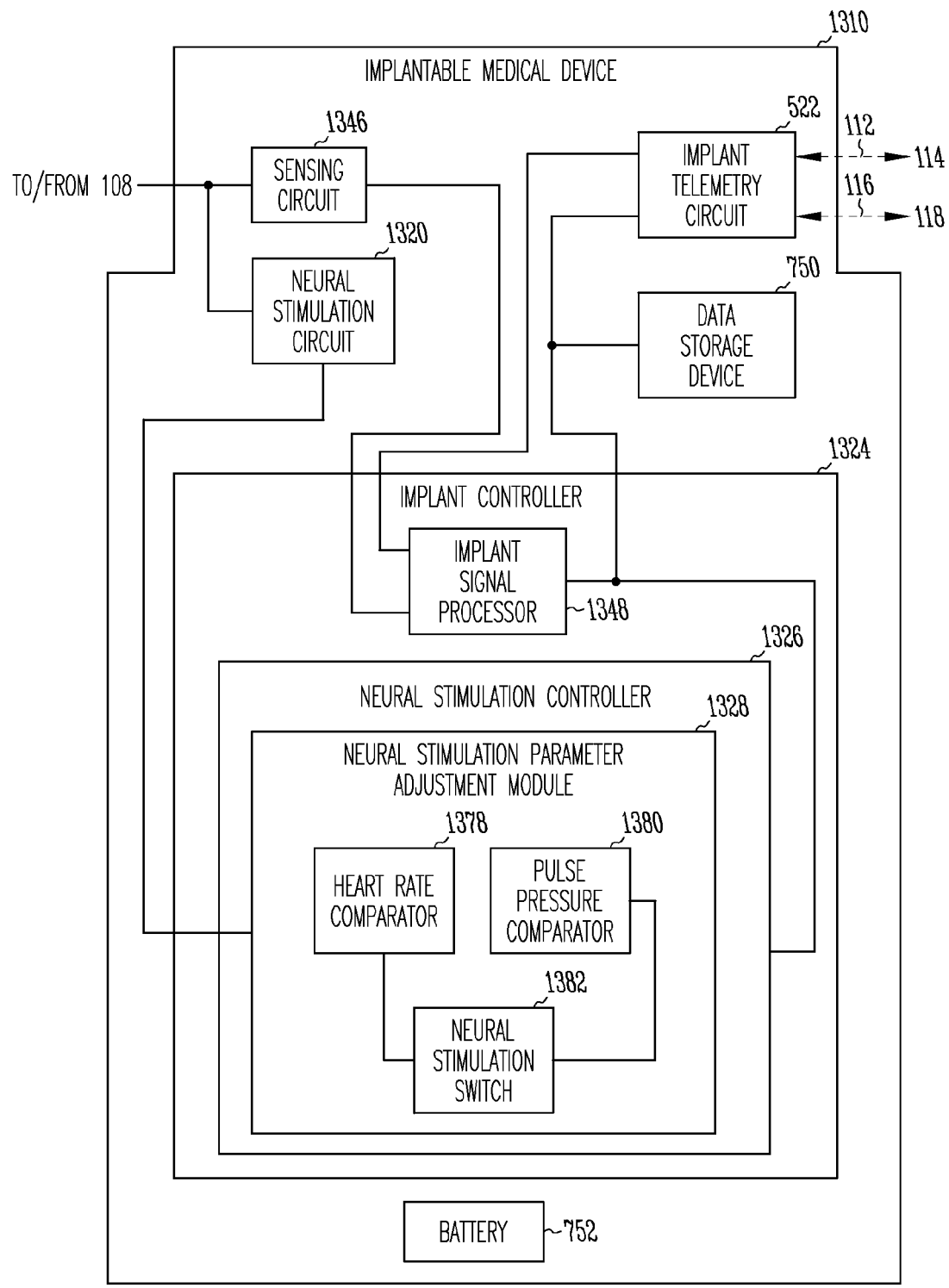
FIG. 13 is a block diagram illustrating an embodiment of portions of a circuit of an implantable medical device that controls neural stimulation using a hemodynamic signal sensed by a non-invasive hemodynamic sensor.

FIG. 13 is a block diagram illustrating an embodiment of portions of a circuit of an implantable medical device 1310, which is a specific embodiment of implantable medical device 110. Implantable medical device 1310 controls neural stimulation using the hemodynamic signal sensed by non-invasive hemodynamic sensing device 114. In one embodiment, non-invasive hemodynamic sensing device 114 provides for sensing of one or more cardiac performance parameters when a direct connection to heart 101 is not needed for delivering the neural stimulation pulses and therefore unavailable. In a specific embodiment, in which neural stimulation is applied to lower blood pressure, non-invasive hemodynamic sensing device 114 includes a cuff pressure sensor configured as an arm band or wrist band to sense a peripheral blood pressure signal from which systolic pressure, diastolic pressure, and/or pulse pressure are measured. Implantable medical device 1310 includes a sensing circuit 1346, a neural stimulation circuit 1320, implant telemetry circuit 522, data storage device 750, implant controller 1324, and battery 752.

Sensing circuit 1346 is a specific embodiment of sensing circuit 746 and senses one or more cardiac and/or neural signals for neural stimulation control. Neural stimulation circuit 1320 is a specific embodiment of electrical stimulation circuit 520 and delivers neural stimulation pulses to one or more nerves of body 102, such as one or more nerves of the autonomic nervous system, through lead system 108.

Implant controller 1324 includes an implant signal processor 1348 and a neural stimulation controller 1326. Implant signal processor 1348 processes the one or more cardiac and/or neural signals for use by neural stimulation controller 1326 and provides neural stimulation controller 1326 with one or more cardiac performance parameters that are received from non-invasive hemodynamic sensing device 114 or produced from the hemodynamic data received from non-invasive hemodynamic sensing device 114. Neural stimulation controller 1326 controls the delivery of neural stimulation pulses using one or more neural stimulation parameters and includes a neural stimulation parameter adjustment module 1328. Neural stimulation parameter adjustment module 1328 adjusts the one or more neural stimulation parameters using the one or more cardiac performance parameters. In one embodiment, neural stimulation parameter adjustment module 1328 sets the one or more neural stimulation parameters to prevent ventricular remodeling or to decrease the heat rate and/or blood pressure when the heart rate parameter is above the predetermined threshold heart rate and/or when the pulse pressure parameter is above the predetermined threshold pulse pressure.

In one embodiment, as illustrated in FIG. 13, neural stimulation parameter adjustment module 1328 includes a heart rate comparator 1378, a pulse pressure comparator 1380, and a neural stimulation switch 1382. In other embodiments, neural stimulation parameter adjustment module 1328 includes any one of heart rate comparator 1378 and pulse pressure comparator 1380. Neural stimulation switch 1382 allows for starting, stopping, and adjustment of the delivery of the neural stimulation pulses using any one or both of the heart rate parameter and the pulse pressure parameter. Heart rate comparator 1378 compares the heart rate parameter to a predetermined threshold heart rate. In a specific embodiment, neural stimulation switch 1382 stops the delivery of the neural stimulation pulses when the heart rate parameter is below the predetermined threshold heart rate. In another specific embodiment, neural stimulation switch 1382 stops the delivery of the neural stimulation pulses when the heart rate parameter drops below a first predetermined threshold heart rate and starts the delivery of the neural stimulation pulses when the heart rate rises above a second predetermined threshold heart rate. The first predetermined threshold heart rate is lower than the second predetermined threshold heart rate. Pulse pressure comparator 1380 compares the pulse pressure parameter to a predetermined threshold pulse pressure. In a specific embodiment, neural stimulation switch 1382 stops the delivery of the neural stimulation pulses when the pulse pressure parameter is below the predetermined threshold pulse pressure. In another specific embodiment, neural stimulation switch stops the delivery of the neural stimulation pulses when the pulse pressure parameter drops below a first predetermined threshold pulse pressure and starts the delivery of the neural stimulation pulses when the pulse pressure parameter rises above a second predetermined threshold pulse pressure. The first predetermined threshold pulse pressure is lower than the second predetermined threshold pulse pressure.

Figure 14:
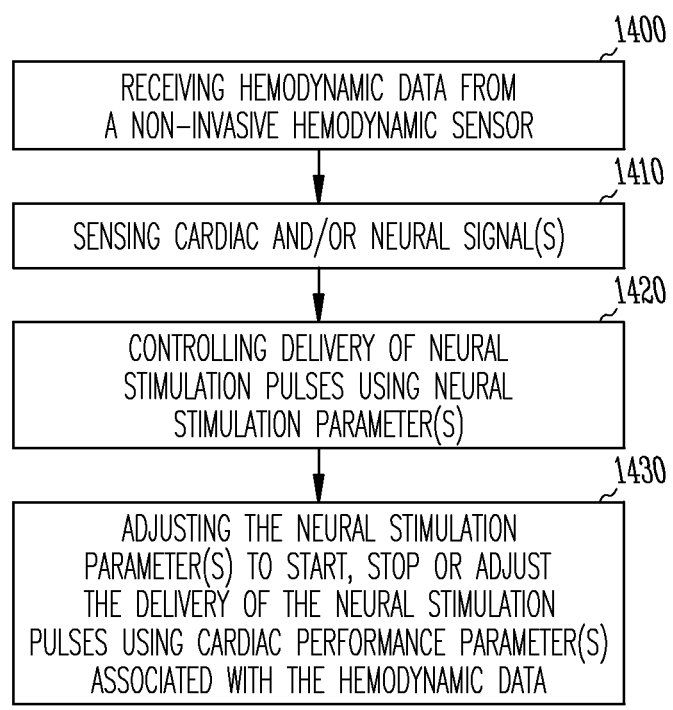
FIG. 14 is a flow chart illustrating a method for controlling neural stimulation using a non-invasive hemodynamic sensing device and an implantable medical device.

FIG. 14 is a flow chart illustrating a method for controlling neural stimulation using a non-invasive hemodynamic sensor and an implantable medical device. In one embodiment, the non-invasive hemodynamic sensor is non-invasive hemodynamic sensing device 114, including any of its specific embodiments, and the implantable medical device is implantable medical device 1310.

Hemodynamic data are received from the non-invasive hemodynamic sensor at 1400. In one embodiment, the hemodynamic data include data representative of one or more cardiac performance parameters. In another embodiment, the hemodynamic data include data representative of the sensed hemodynamic signal, and the implantable medical device produces the one or more cardiac performance parameters using the data representative of the sensed hemodynamic signal. One or more cardiac and/or neural signals are sensed at 1410 for neural stimulation control. Delivery of neural stimulation pulses is controlled using one or more neural stimulation parameters at 1420. The one or more neural stimulation parameters are adjusted to start, stop, or adjust the delivery of the neural stimulation pulses using the hemodynamic data, including the one or more cardiac performance parameters, at 1430. In one embodiment, the one or more neural stimulation parameters are set to prevent ventricular remodeling or to decrease the heat rate and/or blood pressure when the heart rate parameter and/or the pulse pressure parameter indicates that the patient's cardiac output is at a tolerable level.

In one embodiment of step 1430, the heart rate parameter is compared to a predetermined threshold heart rate. In a specific embodiment, the delivery of the neural stimulation pulses is stopped when the heart rate parameter is below the predetermined threshold heart rate. In another specific embodiment, the delivery of the neural stimulation pulses is stopped when the heart rate parameter drops below a first predetermined threshold heart rate and started when the heart rate rises above a second predetermined threshold heart rate. The first predetermined threshold heart rate is lower than the second predetermined threshold heart rate. The pulse pressure parameter is compared to a predetermined threshold pulse pressure. In a specific embodiment, the delivery of the neural stimulation pulses is stopped when the pulse pressure parameter is below the predetermined threshold pulse pressure. In another specific embodiment, the delivery of the neural stimulation pulses is stopped when the pulse pressure parameter drops below a first predetermined threshold pulse pressure and started when the pulse pressure parameter rises above a second predetermined threshold pulse pressure. The first predetermined threshold pulse pressure is lower than the second predetermined threshold pulse pressure.

Example 3

Cardiac Performance Optimization

In one embodiment, CRM system 100 provides cardiac performance feedback control to a cardiac stimulation therapy to optimize cardiac output. For example, while delivering CRT, cardiac output is to be optimized by approximately maximizing a peripheral pulse pressure measured by a non-invasive hemodynamic sensor.

Figure 15:
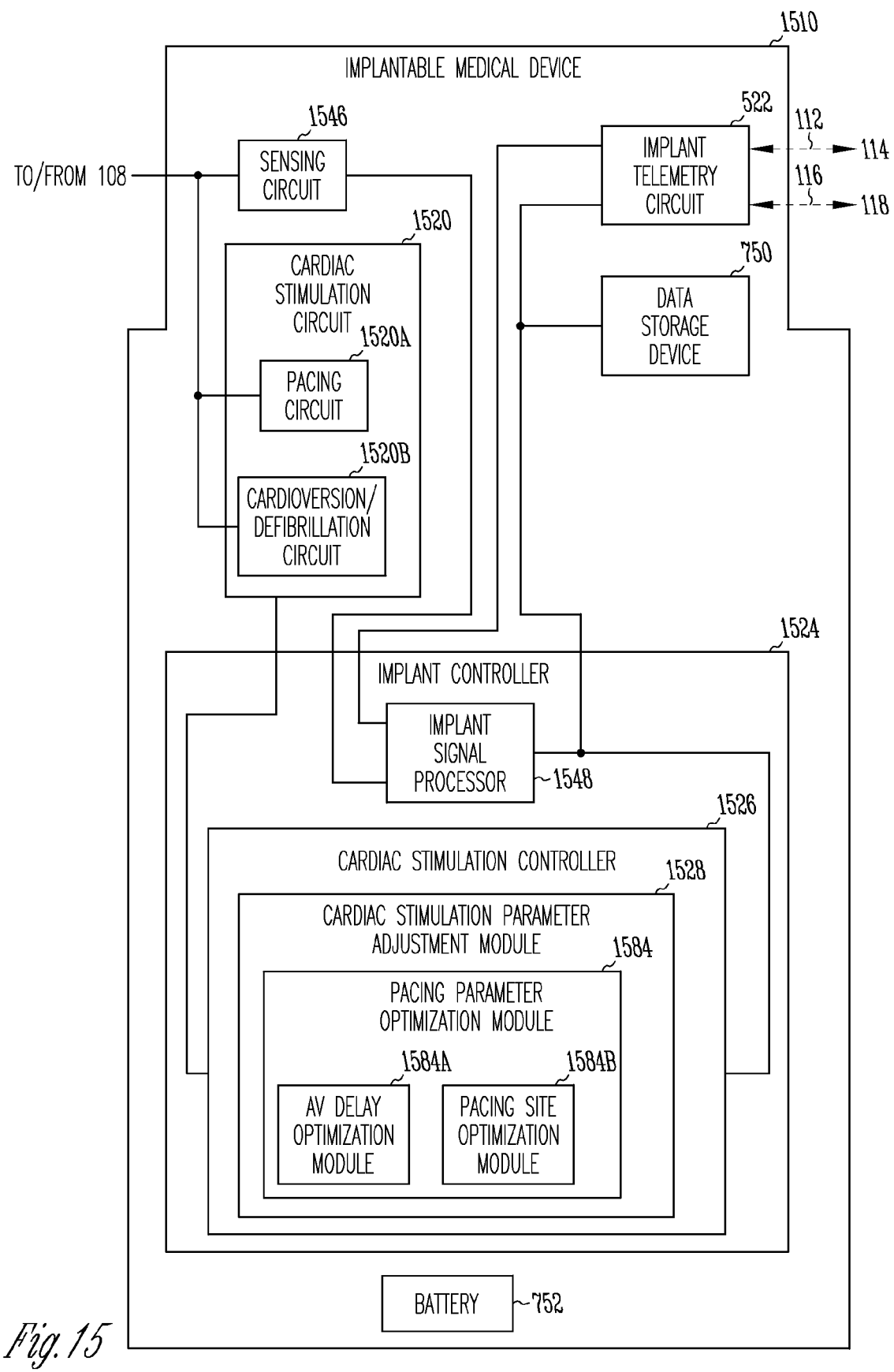
FIG. 15 is a block diagram illustrating an embodiment of portions of a circuit of an implantable medical device that controls a cardiac therapy to optimize a cardiac performance parameter using a hemodynamic signal sensed by a non-invasive hemodynamic sensor.

FIG. 15 is a block diagram illustrating an embodiment of portions of a circuit of an implantable medical device 1510, which is a specific embodiment of implantable medical device 110. Implantable medical device 1510 controls a cardiac therapy to optimize one or more cardiac performance parameters using the hemodynamic signal sensed by non-invasive hemodynamic sensing device 114. Implantable medical device 1510 includes a sensing circuit 1546, a cardiac stimulation circuit 1520, implant telemetry circuit 522, data storage device 750, implant controller 1524, and battery 752.

Sensing circuit 1546 is a specific embodiment of sensing circuit 746 and senses one or more electrograms for control of cardiac stimulation including pacing and cardioversion/defibrillation. Cardiac stimulation circuit 1520 is a specific embodiment of electrical stimulation circuit 520 and includes a pacing circuit 1520A and a cardioversion/defibrillation circuit 1520B. Pacing circuit 1520A delivers pacing pulses to heart 101 though lead system 108. Cardioversion/defibrillation circuit 1520B delivers cardioversion/defibrillation circuit pulses to heart 101 through lead system 108.

Implant controller 1524 includes an implant signal processor 1548 and a cardiac stimulation controller 1526. Implant signal processor 1548 processes the one or more electrograms for use by cardiac stimulation controller 1526 and provides cardiac stimulation controller 1526 with one or more cardiac performance parameters that are received from non-invasive hemodynamic sensing device 114 or produced from the hemodynamic data received from non-invasive hemodynamic sensing device 114. Cardiac stimulation controller 1526 controls the delivery of the pacing pulses using one or more pacing parameters and the delivery of the cardioversion/defibrillation pulses using one or more cardioversion/defibrillation parameters. Cardiac stimulation controller 1526 includes a cardiac stimulation parameter adjustment module 1528 that adjusts the one or more pacing parameters and the one or more cardioversion/defibrillation parameters using the one or more cardiac performance parameters. In one embodiment, cardiac stimulation adjustment module 1528 adjusts the one or more pacing parameters to approximately optimize a measure of cardiac function indicated by one of the one or more cardiac performance parameters. In one embodiment, cardiac stimulation adjustment module 1528 adjusts the one or more cardioversion/defibrillation parameters to select an approximately optimal type and/or energy level for a cardioversion/defibrillation pulse according to the patient's hemodynamic performance during a detected tachyarrhythmia episode as measured by the one or more cardiac performance parameters.

In one embodiment, as illustrated in FIG. 15, cardiac stimulation parameter optimization module 1528 includes a pacing parameter optimization module 1584 that approximately optimizes the one or more pacing parameters using the pulse pressure parameter. Pacing parameter optimization module 1584 includes an atrioventricular (AV) delay optimization module 1584A and a pacing site optimization module 1584B. AV delay optimization module 1584A approximately optimizes one or more AV delays to maximize the value of the pulse pressure parameter. In a specific embodiment, cardiac stimulation controller 1526 controls the delivery of the pacing pulses using a plurality of AV delays provided by AV delay optimization module 1584A and collects a plurality of values for the pulse pressure parameter each corresponding to one of the AV delays. AV delay optimization module 1584A selects an optimal AV delay, such as the AV delay that corresponds to the maximum collected value for the pulse pressure parameter or the shortest AV delay that does not cause a decrease in the value of the pulse pressure parameter. In a further specific embodiment, in addition to the AV delays, cardiac stimulation controller 1526 controls the delivery of the pacing pulses using a plurality of interventricular (IV) delays. AV delay optimization module 1584A selects an optimal AV delay and an optimal IV delay. In another specific embodiment, the pacing pulses are delivered to two or more ventricular sites through lead system 108. Cardiac stimulation controller 1526 controls the delivery of the pacing pulses using a plurality of different pacing sites and/or combinations of pacing sites provided by pacing site optimization module 1584B and collects a plurality of values for the pulse pressure parameter each corresponding to one of the pacing sites and/or combinations of pacing sites. Pacing site optimization module 1584B selects the pacing site or combination of pacing sites corresponding to the maximum collected value for the pulse pressure parameter as the optimal pacing site or optimal combination of pacing sites. In another specific embodiment, cardiac stimulation controller 1526 controls the delivery of the pacing pulses using a plurality of parameter combinations of two or more of AV delays, IV delays, and pacing cites provided by pacing parameter optimization module 1584 and collects a plurality of values for the pulse pressure parameter each corresponding to one of the parameter combinations. Pacing parameter optimization module 1584 selects an optimal combination of an AV delay and one or more pacing sites, such as the combination corresponding to the maximum collected value for the pulse pressure parameter.

Figure 16:
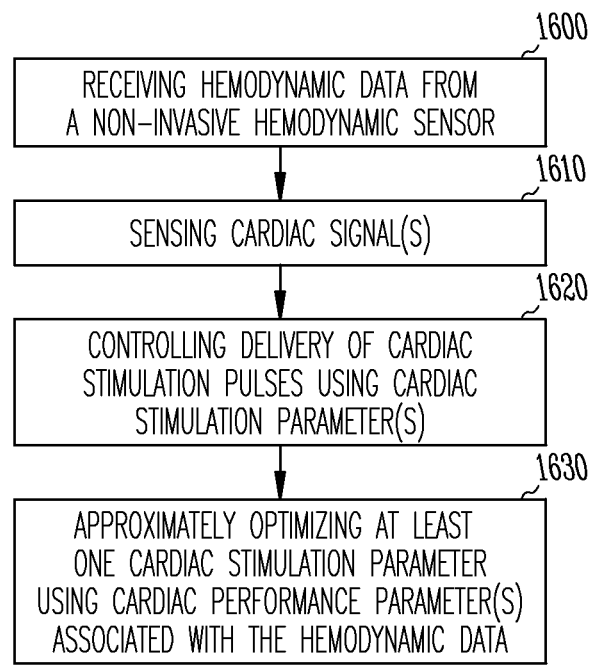
FIG. 16 is a flow chart illustrating a method for controlling a cardiac therapy to optimize a cardiac performance parameter using a non-invasive hemodynamic sensing device and an implantable medical device.

FIG. 16 is a flow chart illustrating a method for controlling a cardiac therapy to optimize a cardiac performance parameter using a non-invasive hemodynamic sensor and an implantable medical device. In one embodiment, the non-invasive hemodynamic sensor is non-invasive hemodynamic sensing device 114, including any of its specific embodiments, and the implantable medical device is implantable medical device 1510.

Hemodynamic data are received from the non-invasive hemodynamic sensor at 1600. In one embodiment, the hemodynamic data include data representative of one or more cardiac performance parameters. In another embodiment, the hemodynamic data include data representative of the sensed hemodynamic signal, and the implantable medical device produces the one or more cardiac performance parameters using the data representative of the sensed hemodynamic signal. One or more cardiac signals such as electrograms are sensed at 1610 for cardiac stimulation control. Delivery of cardiac stimulation pulses, such as pacing pulses and cardioversion/defibrillation pulses, is controlled using one or more cardiac stimulation parameters, such as pacing parameters and cardioversion/defibrillation parameters, at 1620. The one or more cardiac stimulation parameters are adjusted to start, stop, or adjust the delivery of the cardiac stimulation pulses using the one or more cardiac performance parameters at 1630. In one embodiment, one or more pacing parameters are adjusted to approximately optimize a measure of cardiac function indicated by one of the one or more cardiac performance parameters. In one embodiment, one or more cardioversion/defibrillation parameters are adjusted to select an approximately optimal type and/or energy level for a cardioversion/defibrillation pulse according to the patient's hemodynamic performance during a detected tachyarrhythmia episode as measured by the one or more cardiac performance parameters.

In one embodiment of step 1630, one or more pacing parameters are approximately optimized using the pulse pressure parameter. The one or more pacing parameters include one or more AV delays and/or one or more pacing sites. The one or more AV delays and/or the one or more pacing sites are approximately optimized to provide for an optimal cardiac output as indicated by an approximately maximum value for the pulse pressure parameter. In a specific embodiment, pacing pulses are delivered using a plurality of AV delays, and the value of the pulse pressure parameter corresponding to each of the AV delays is recorded. The AV delay corresponding to the maximum recorded value of the pulse pressure parameter is selected as the optimal AV delay. In another specific embodiment, pacing pulses are delivered using a plurality of different pacing sites and/or combinations of pacing sites, and the value of the pulse pressure parameter corresponding to each of the pacing sites and/or combinations of pacing sites is recorded. The pacing site and/or combination of pacing sites corresponding to the maximum recorded value of the pulse pressure parameter is selected as the optimal pacing site or optimal combination of pacing sites. In other specific embodiments, pacing pulses are delivered using a plurality of parameter combinations of two or more of AV delay, IV delay, and pacing sites. The value of the pulse pressure parameter corresponding to each of the parameter combination is recorded. An optimal parameter combination is selected based on the recorded values of the pulse pressure parameter.

Example 4

Arrhythmia Detection and Treatment

In one embodiment, CRM system 100 provides for detection and treatment of arrhythmias using hemodynamic status of the patient. For example, arrhythmia is detected using heart rate detected from an intracardiac electrogram and/or a hemodynamic signal sensed by a non-invasive hemodynamic sensor. The hemodynamic signal also indicates the patient's hemodynamic performance based on which an appropriate or optimal anti-arrhythmia therapy is determined.

Figure 17:
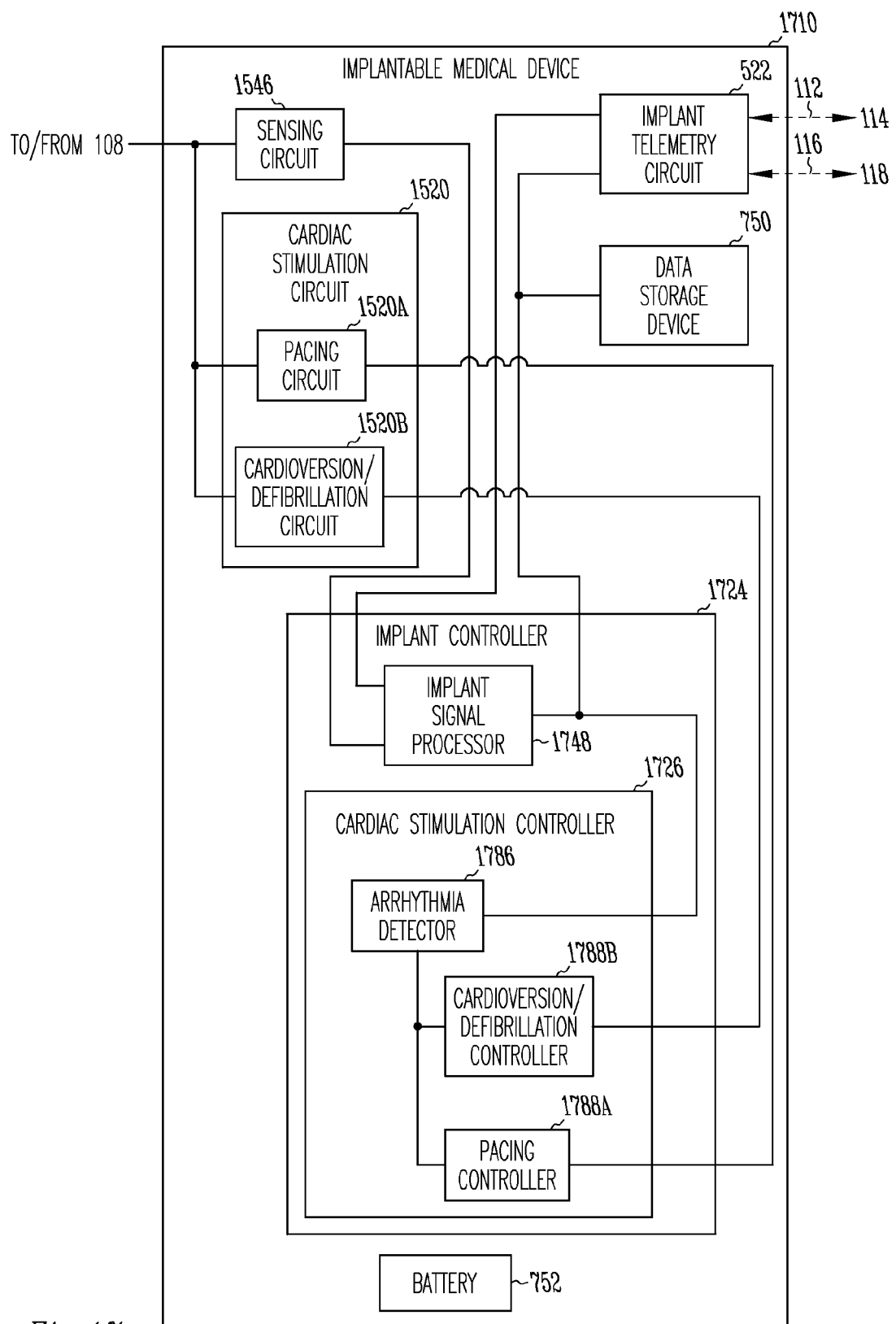
FIG. 17 is a block diagram illustrating an embodiment of portions of a circuit of an implantable medical device that controls arrhythmia treatments using a hemodynamic signal sensed by a non-invasive hemodynamic sensor.

FIG. 17 is a block diagram illustrating an embodiment of portions of a circuit of an implantable medical device 1710. Implantable medical device 1710 is a specific embodiment of implantable medical device 110 and controls arrhythmia detection and treatments using the hemodynamic signal sensed by non-invasive hemodynamic sensing device 114. Implantable medical device 1710 includes a sensing circuit 1546, cardiac stimulation circuit 1520, implant telemetry circuit 522, data storage device 750, implant controller 1724, and battery 752.

Implant controller 1724 includes an implant signal processor 1748 and a cardiac stimulation controller 1726. Implant signal processor 1748 processes the one or more electrograms for use by cardiac stimulation controller 1726 and provides cardiac stimulation controller 1726 with one or more cardiac performance parameters that are received from non-invasive hemodynamic sensing device 114 or produced from the hemodynamic data received from non-invasive hemodynamic sensing device 114. The one or more cardiac performance parameters provide for an indication of the patient's hemodynamic status that allows a determination of a need for, and/or an adequate type of, cardiac stimulation therapy. Examples of such cardiac stimulation therapy include an anti-bradycardia pacing therapy, an anti-tachycardia pacing (ATP) therapy, a cardioversion therapy, and a defibrillation therapy. Cardiac stimulation controller 1726 controls the delivery of the cardiac stimulation pulses using one or more cardiac stimulation parameters.

In one embodiment, as illustrated in FIG. 17, cardiac stimulation controller 1726 includes an arrhythmia detector 1786, a pacing controller 1788A, and a cardioversion/defibrillation controller 1788B. Arrhythmia detector 1786 detects an arrhythmia using the one or more electrograms and/or the one or more cardiac performance parameters. In one embodiment, arrhythmia detector 1786 detects the arrhythmias using the heart rate parameter and the pulse pressure parameter, both derived from the hemodynamic signal. For example, a detection of tachyarrhythmia is declared when the heart rate parameter exceeds a predetermined tachyarrhythmia threshold and the pulse pressure parameter drops below a predetermined threshold pulse pressure. In another embodiment, arrhythmia detector 1786 detects the arrhythmias using the heart rate parameter and classifies each detected arrhythmia using the pulse pressure parameter. For example, a detection of tachyarrhythmia is declared when the heart rate parameter exceeds a predetermined tachyarrhythmia threshold, and the detected arrhythmia is classified by the type of therapy needed according to whether the pulse pressure parameter drops below one or more predetermined threshold pulse pressures. In another embodiment, arrhythmia detector 1786 uses a heart rate parameter representative of a heart rate detected from an electrogram instead of the heart rate parameter derived from the hemodynamic signal. This ensures continuous arrhythmia detection when non-invasive hemodynamic sensing device 114 is not attached to the patient. In one embodiment, arrhythmia detector 1786 uses the one or more electrograms as primary parameters for arrhythmia detection and classification and uses the one or more cardiac performance parameters derived from the hemodynamic signal, when available, as secondary or supplemental parameters for the arrhythmia detection and classification. For example, such secondary or supplemental parameters are used to validate an arrhythmia detection and/or classification, to substitute for the primary parameters when the one or more electrograms are noisy, and/or to provide for a separate signal for detecting ventricular fibrillation (during which electrogram amplitude may be low).

Pacing controller 1788A controls the delivery of pacing pulses according to a bradyarrhythmia pacing mode or an ATP mode. Cardioversion/defibrillation controller 1788B controls the delivery of the cardioversion/defibrillation pulses.

Figure 18:
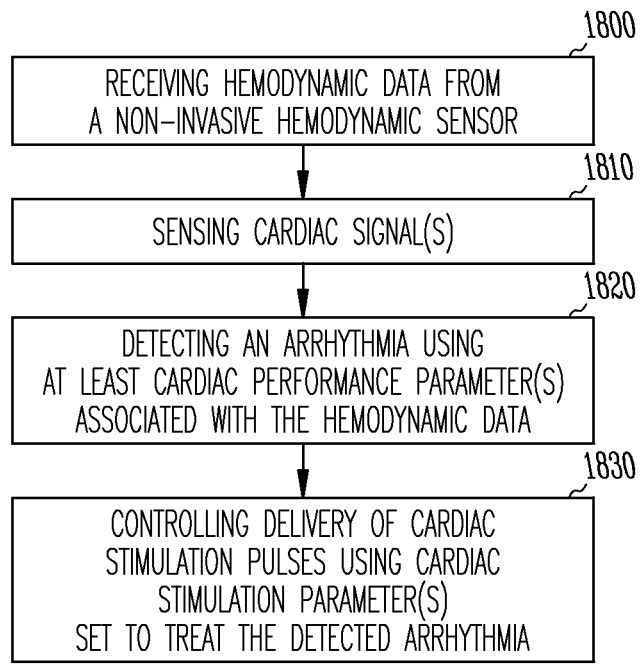
FIG. 18 is a flow chart illustrating a method for detecting and treating arrhythmias using a non-invasive hemodynamic sensing device and an implantable medical device.

FIG. 18 is a flow chart illustrating a method for detecting and treating arrhythmias using a non-invasive hemodynamic sensor and an implantable medical device. In one embodiment, the non-invasive hemodynamic sensor is non-invasive hemodynamic sensing device 114, including any of its specific embodiments, and the implantable medical device is implantable medical device 1710.

Hemodynamic data are received from the non-invasive hemodynamic sensor at 1800. In one embodiment, the hemodynamic data include data representative of one or more cardiac performance parameters. In another embodiment, the hemodynamic data include data representative of the sensed hemodynamic signal, and the implantable medical device produces the one or more cardiac performance parameters using the data representative of the sensed hemodynamic signal. The one or more cardiac performance parameters indicate occurrences of arrhythmia and/or the effect of the arrhythmia on the patient's hemodynamic performance. One or more cardiac signals such as electrograms are sensed at 1810 for cardiac stimulation control and/or arrhythmia detection. An arrhythmia is detected using at least the one or more cardiac performance parameters at 1820. This includes the detection of the occurrence of the arrhythmia and the classification of the arrhythmia based on the associated hemodynamic performance. Delivery of cardiac stimulation pulses, such as pacing pulses and cardioversion/defibrillation pulses, is controlled using one or more cardiac stimulation parameters, such as pacing parameters and cardioversion/defibrillation parameters, to treat the detected arrhythmia at 1830. The cardiac stimulation parameters are selected or adjusted to treat the detected arrhythmia by delivering, for example, an anti-bradyarrythmia pacing therapy, an ATP therapy, or a cardioversion/defibrillation therapy.

In one embodiment of step 1820, the arrhythmia is detected using the heart rate parameter and the pulse pressure parameter, both derived from the hemodynamic signal. In one embodiment, the detection of tachyarrhythmia is declared when the heart rate parameter exceeds a predetermined tachyarrhythmia threshold and the pulse pressure parameter drops below a predetermined threshold pulse pressure. In another embodiment, the detection of tachyarrhythmia is declared when the heart rate parameter exceeds the predetermined tachyarrhythmia threshold, and the arrhythmia is classified by comparing the pulse pressure parameter to one or more predetermined threshold pulse pressures. In another embodiment of step 1820, a heart rate parameter detected from an electrogram is used instead of the heart rate parameter derived from the hemodynamic signal. In one embodiment, one or more signals sensed by the implantable medical device, such as one or more electrograms, are used as primary signal(s) for the arrhythmia detection and classification. The hemodynamic signal sensed by the non-invasive hemodynamic sensor, when available, is used as a secondary or supplemental signal for the arrhythmia detection and/or classification.

Example 5

Diagnostics

In one embodiment, CRM system 100 provides patient diagnostic data on peripheral blood pressure and oxygen saturation changes over a period of time, with information on associated therapy settings when one or more therapies are delivered during that period of time. This provides a physician or other caregiver with information indicative of a patient's cardiac functions, including cardiac functions in association with various physical activities and therapies.

Figure 19:
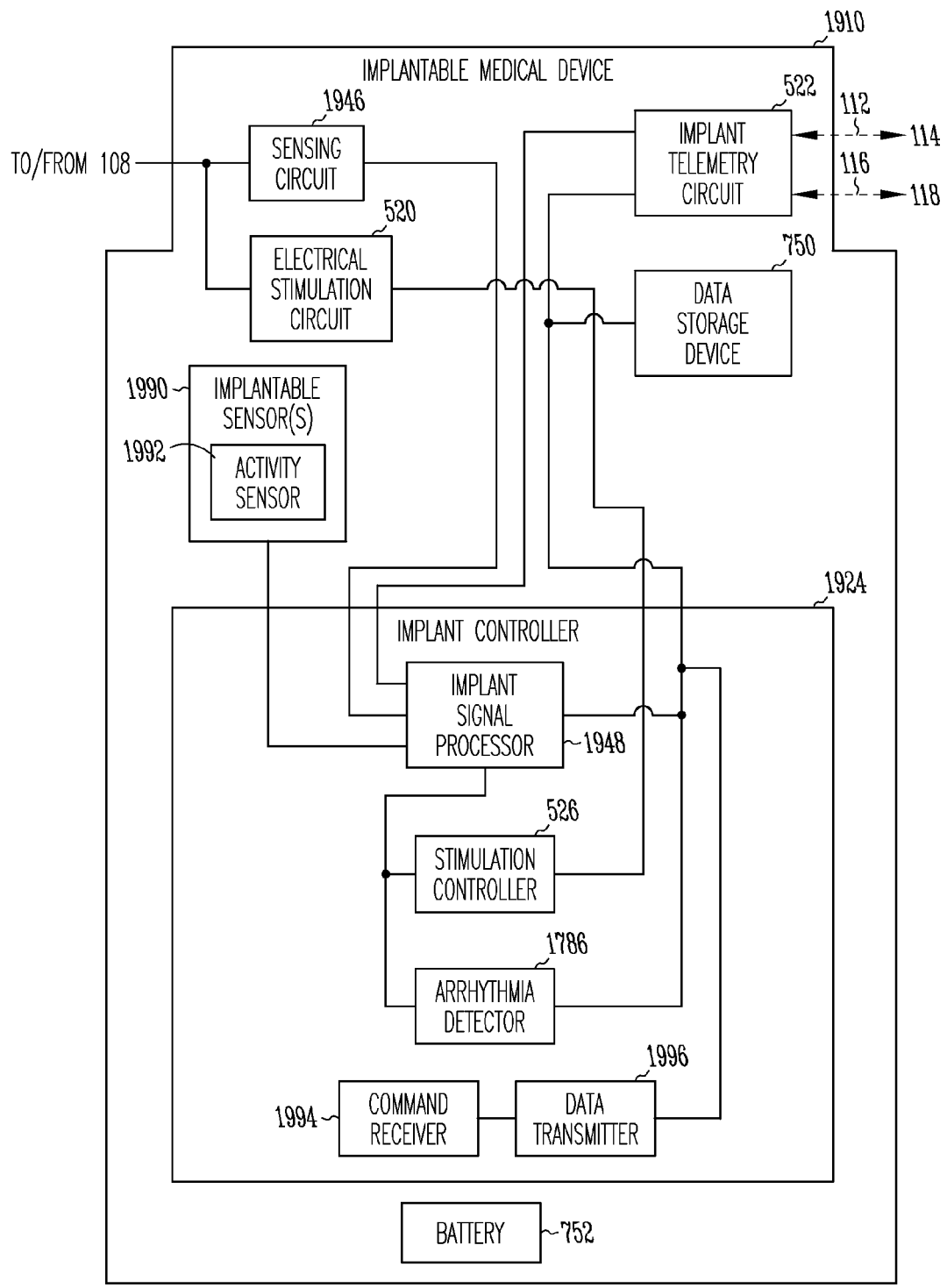
FIG. 19 is a block diagram illustrating an embodiment of portions of a circuit of an implantable medical device providing for acquisition of hemodynamic information associated with a hemodynamic signal sensed by a non-invasive hemodynamic sensor.

FIG. 19 is a block diagram illustrating an embodiment of portions of a circuit of an implantable medical device 1910, which is a specific embodiment of implantable medical device 110. Implantable medical device 1910 provides for acquisition of hemodynamic information associated with the hemodynamic signal sensed by non-invasive hemodynamic sensing device 114 as well as other information associated with the patient's physiological conditions and/or physical activities. Such information is transmitted to external system 118 to allow for diagnosis and adjustment of therapy settings with or without the patient's presence before the physician or other caregiver. Implantable medical device 1910 includes a sensing circuit 1946, electrical stimulation circuit 520, implant telemetry circuit 522, one or more implantable sensors 1990, data storage device 750, implant controller 1924, and battery 752.

Sensing circuit 1946 senses one or more cardiac and/or neural signals through lead system 108. Implantable sensor(s) 1990 sense each sense a signal indicative of the patient's cardiac function or another type of signal used in assessment of the patient's cardiac function. In various embodiments, implantable sensor(s) 1990 are each included within implantable medical device 1910, incorporated onto the housing of implantable medical device 1910, or connected to implantable medical device 1910 through lead system 108 or another lead or cable. In one embodiment, as illustrated in FIG. 19, implantable sensor(s) 1990 include an activity sensor 1992 to sense the patient's level of gross physical activity, which is used in assessment of the patient's cardiac function. In a specific embodiment, activity sensor 1992 includes an accelerometer. In various other embodiments, implantable sensor(s) 1990 include one or more of impedance sensors, acoustic sensors, posture sensors, pressure sensors, blood electrolyte sensors, and blood gas sensors.

Implant controller 1924 includes an implant signal processor 1948, stimulation controller 526, arrhythmia detector 1786, a command receiver 1994, and a data transmitter 1996. Implant signal processor 1948 processes the one or more cardiac and/or neural signals, processes the one or more signals sensed by the one or more implantable sensors 1990, and provides stimulation controller 526 with one or more cardiac performance parameters that are received from non-invasive hemodynamic sensing device 114 or produced from the hemodynamic signal received from non-invasive hemodynamic sensing device 114. Data storage device 750 stores data representative of the hemodynamic signal and/or data representative of the one or more cardiac performance parameters. Such stored data include data representative of the pulse pressure parameter, data representative of the blood oxygen saturation parameter, and data representative of the heart rate parameter. In various embodiments, data storage device 750 also stores, for example, data representative of the cardiac and/or neural signal(s), data representative of the activity level, data representative the information about each of the detected arrhythmia episodes, and data representative of therapy settings and history, including the one or more stimulation parameters. Command receiver 1994 receives a data retrieval command entered by the physician or other caregiver through external system 118 and telemetry link 116. Data transmitter 1996 retrieves data from data storage device 750 according to the data retrieval command and causes implant telemetry circuit 522 to transmit the retrieved data to external system 118 through telemetry link 116.

Figure 20:
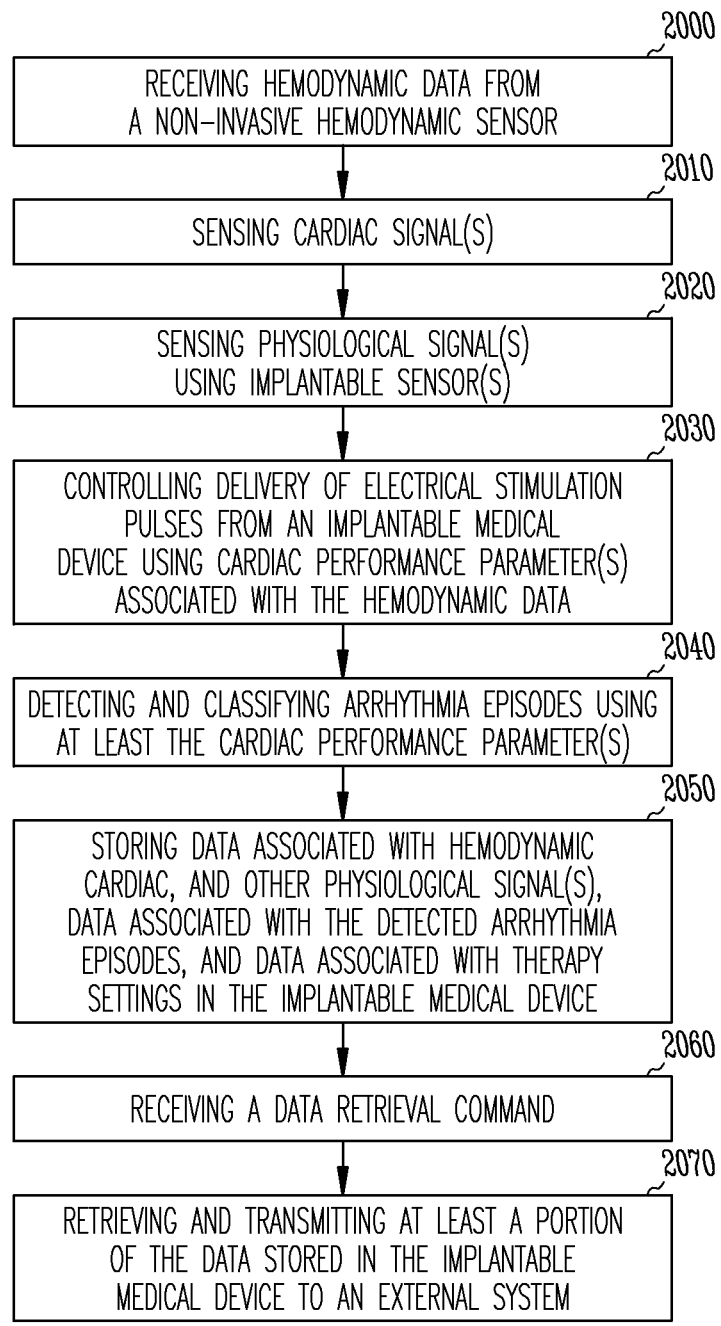
FIG. 20 is a flow chart illustrating a method for acquiring diagnostic data using a non-invasive hemodynamic sensing device and an implantable medical device.

FIG. 20 is a flow chart illustrating a method for acquiring diagnostic data using a non-invasive hemodynamic sensor and an implantable medical device. In one embodiment, the non-invasive hemodynamic sensor is non-invasive hemodynamic sensing device 114, including any of its specific embodiments, and the implantable medical device is implantable medical device 1910.

Hemodynamic data are received from the non-invasive hemodynamic sensor at 2000. In one embodiment, the hemodynamic data include data representative of one or more cardiac performance parameters. In another embodiment, the hemodynamic data include data representative of the sensed hemodynamic signal, and the implantable medical device produces the one or more cardiac performance parameters using the data representative of the sensed hemodynamic signal. The one or more cardiac performance parameters indicate occurrences of arrhythmia and/or the effect of the arrhythmia on the patient's hemodynamic performance. Examples of the one or more cardiac performance parameters include the pulse pressure parameter, the blood oxygen saturation parameter, and the heart rate parameter.

One or more cardiac signals such as electrograms are sensed at 2010 for cardiac stimulation control, arrhythmia detection, and/or patient monitoring purposes. One or more physiological signals are sensed using one or more implantable sensors at 2020. Examples of such one or more physiological signals includes neural signals, activity level signals, respiratory signals, cardiac or transthoracic impedance signals, heart sound signals, pressure signals, and signals indicative of blood chemistry. Such signals allow for assessment of the patient's cardiac function based on the hemodynamic signal and various factors having influence on the hemodynamic signal. Data representative of the hemodynamic signal and/or the cardiac performance parameter(s) as well as data representative of the physiological signal(s) and parameter(s) derived from the physiological signal(s) are produced for storage in the implantable medical device.

In one embodiment, delivery of electrical stimulation pulses from the implantable medical device is controlled using at least the one or more cardiac performance parameters at 2030. For example, one or more stimulation parameters are adjusted using the one or more cardiac performance parameters, and the electrical stimulation pulses are delivered according to the one or more stimulation parameters. Data representative of therapeutic settings, including values of the one or more stimulation parameters used, are produced for storage in the implantable medical device.

Arrhythmia episodes are detected and classified using at least the one or more cardiac performance parameters at 2040. In one embodiment, arrhythmia episodes are detected using the heart rate parameter and classified using the pulse pressure parameter. The classification provides for a basis for determining an appropriate therapy. In another embodiment, arrhythmia episodes are detected using the heart rate derived from a cardiac signal such as an electrogram and classified using the pulse pressure parameter. In one embodiment, the one or more cardiac signals are primary signals used for arrhythmia detection and classification, while the one or more cardiac performance parameters are used as secondary or supplemental signals for the arrhythmia detection and classification. Data representative of information about each of the detected arrhythmia episodes are produced for storage in the implantable medical device.

Data associated with the hemodynamic, cardiac, and other physiological signals, data associated with the detected arrhythmia episodes, and data associated with the therapy setting are stored in the implantable medical device at 2050. A data retrieval command is received at 2060. In one embodiment, the data retrieval command is indicative of the type of data to be retrieved from the implantable medical device. In response to the data retrieval command, at least a portion of the data stored in the implantable medical device is retrieved and transmitted from the implantable medical device to an external system at 2070. The retrieved and transmitted data provide for bases for diagnosing or monitoring the patient's cardiac functions and for making therapeutic decisions.

In General

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A system adapted to be coupled to a body having external appendages including a finger, a toe, an ear, an arm, and a wrist, the system comprising:
   a non-invasive hemodynamic sensing device including at least a portion configured to be attached to one of the external appendages, the non-invasive hemodynamic sensing device configured to sense a hemodynamic signal indicative of at least a heart rate, produce hemodynamic data associated with the hemodynamic signal, and transmit the hemodynamic data; and
   an implantable medical device configured to be communicatively coupled to the non-invasive hemodynamic sensing device via a wireless communication link to receive the hemodynamic data, the implantable medical device including:
      a neural stimulation circuit configured to deliver neural stimulation pulses; and
      a neural stimulation controller configured to control the delivery of the neural stimulation pulses using one or more neural stimulation parameters tier treating a cardiovascular disorder, the neural stimulation controller including a stimulation parameter adjustment module configured to adjust the one or more neural stimulation parameters using one or more cardiac performance parameters, the stimulation parameter adjustment module configured to compare a heart rate parameter representative of the heart rate to a predetermined threshold heart rate and adjust the delivery of the neural stimulation pulses using an outcome of the comparison,
   wherein one of the non-invasive hemodynamic sensing device and the implantable medical device includes a parameter generator configured to produce the one or more cardiac performance parameters including the heart rate parameter using the hemodynamic data.

2. The system of claim 1, wherein the stimulation parameter adjustment module is configured to set the one or more neural stimulation parameters to prevent ventricular remodeling.

3. The system of claim 1, wherein the stimulation parameter adjustment module is configured to set the one or more neural stimulation parameters to decrease blood pressure.

4. The system of claim 3, wherein the non-invasive hemodynamic sensing device comprises a cuff sensor configured for attachment to the arm or the wrist to sense a peripheral blood pressure signal.

5. The system of claim 1, wherein the parameter generator is further configured to produce a pulse pressure parameter of the one or more cardiac performance parameters, the pulse pressure parameter representative of a pulse pressure, and the stimulation parameter adjustment module is configured to compare the pulse pressure parameter to a predetermined threshold pulse pressure and adjust the delivery of the neural stimulation pulses using an outcome of the comparison of the pulse pressure parameter to the predetermined threshold pulse pressure.

6. The system of claim 5, wherein the stimulation parameter adjustment module comprises a pulse comparator configured to compare the pulse pressure parameter to the predetermined threshold pulse pressure, and the neural stimulation switch is further configured to stop the delivery of the neural stimulation pulses in response to the pulse pressure parameter dropping below the predetermined threshold pulse pressure.

7. The system of claim 1, wherein the stimulation parameter adjustment module comprises a heart rate comparator configured to compare the heart rate parameter representative of the heart rate to the predetermined threshold heart rate and a neural stimulation switch configured to stop the delivery of the neural stimulation pulses in response to the heart rate parameter being below the predetermined threshold heart rate.

8. The system of claim 7, wherein the neural stimulation switch is configured to stop the delivery of the neural stimulation pulses in response to the heart rate parameter dropping below a first predetermined threshold heart rate and start the delivery of the neural stimulation pulses in response to the heart rate rising above a second predetermined threshold heart rate.

9. The system of claim 1, wherein the non-invasive hemodynamic sensing device comprises a clip sensor configured for attachment to the finger, the toe, or the ear.

10. The system of claim 9, wherein the non-invasive hemodynamic sensing device comprises a portable repeater coupled to the clip sense sensor, the portable repeater configured to transmit the hemodynamic data to the implantable medical device via the wireless communication link.

11. A method for delivering electrical stimulation to a patient, the method comprising:
   sensing a hemodynamic signal indicative of at least a heart rate using a non-invasive hemodynamic sensing device;
   producing hemodynamic data associated with the hemodynamic signal;
   transmitting the hemodynamic data to an implantable medical device through a wireless communication link;
   producing one or more cardiac performance parameters including a heart rate parameter representative of the heart rate using the hemodynamic data using one of the non-invasive hemodynamic sensing device and the implantable medical device;
   adjusting one or more neural stimulation parameters using the one or more cardiac performance parameters using a stimulation controller of the implantable medical device;
   controlling delivery of neural stimulation pulses using the one or more stimulation parameters, including comparing the heart rate parameter representative to a predetermined threshold heart rate and adjusting the delivery of the neural stimulation pulses using an outcome of the comparison; and
   delivering the neural stimulation pulses from the implantable medical device.

12. The method of claim 11, wherein delivering the neural stimulation pulses comprises delivering the neural stimulation pulses to a vagus nerve.

13. The method of claim 12, wherein controlling the delivery of the neural stimulation pulses comprises setting the one or more neural stimulation parameters to prevent ventricular remodeling.

14. The method of claim 12, wherein controlling the delivery of the neural stimulation pulses comprises setting the one or more neural stimulation parameters to decrease blood pressure.

15. The method of claim 11, wherein producing the one or more cardiac performance parameters further comprises producing a pulse pressure parameter representative of a pulse pressure, and controlling the delivery of the neural stimulation pulses comprises comparing the pulse pressure parameter to a predetermined threshold pulse pressure and adjusting the delivery of the neural stimulation pulses using an outcome of the comparison of the pulse pressure parameter to the predetermined threshold pulse pressure.

16. The method of claim 15, wherein controlling the delivering of the neural stimulation pulses comprises stopping the delivery of the neural stimulation pulses in response to the pulse pressure parameter dropping below the predetermined threshold pulse pressure.

17. The method of claim 11, wherein controlling the delivery of the neural stimulation pulses comprises stopping the delivery of the neural stimulation pulses in response to the heart rate parameter being below the predetermined threshold heart rate.

18. The method of claim 17, wherein controlling the delivery of the neural stimulation pulses further comprises stopping the delivery of the neural stimulation pulses in response to the heart rate parameter dropping below a first predetermined threshold heart rate and starting the delivery of the neural stimulation pulses in response to the heart rate rising above a second predetermined threshold heart rate.

19. The method of claim 11, comprising sensing the hemodynamic signal when the noninvasive hemodynamic sensing device is attached to the patient's finger, toe, ear, arm, or wrist.

20. The method of claim 19, further comprising controlling the delivery of the neural stimulation pulses for delivering the neural stimulation pulses when the one or more cardiac performance parameters indicate that the patient's cardiac output is at a tolerable level.

* * * * *